US008686141B2

(12) United States Patent
Humphrey et al.

(10) Patent No.: US 8,686,141 B2
(45) Date of Patent: Apr. 1, 2014

(54) PROCESS FOR PREPARING N-SUBSTITUTED HYDROXYPYRIMIDINONE CARBOXAMIDES

(75) Inventors: Guy R. Humphrey, Hillsborough, NJ (US); Ross A. Miller, Fanwood, NJ (US); Peter E. Maligres, Fanwood, NJ (US); Steven Weissman, Short Hills, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 479 days.

(21) Appl. No.: 12/811,254

(22) PCT Filed: Dec. 22, 2008

(86) PCT No.: PCT/US2008/087929
§ 371 (c)(1),
(2), (4) Date: Jun. 30, 2010

(87) PCT Pub. No.: WO2009/088729
PCT Pub. Date: Jul. 16, 2009

(65) Prior Publication Data
US 2010/0280244 A1 Nov. 4, 2010

Related U.S. Application Data

(60) Provisional application No. 61/010,421, filed on Jan. 8, 2008.

(51) Int. Cl.
C07D 239/52 (2006.01)
C07D 413/12 (2006.01)

(52) U.S. Cl.
USPC ........................................................ 544/319

(58) Field of Classification Search
USPC ........................................................ 544/319
See application file for complete search history.

(56) References Cited

U.S. PATENT DOCUMENTS

| 7,169,780 B2 | 1/2007 | Crescenzi et al. |
| 2006/0122205 A1 | 6/2006 | Belyk et al. |

FOREIGN PATENT DOCUMENTS

| WO | 03/035077 A1 | 5/2003 |
| WO | 2006/060730 A2 | 6/2006 |

OTHER PUBLICATIONS

Summa et al., "Discovery of Raltegravir, a Potent, Selective Orally Bioavailable HIV-Integrase Inhibitor for the Treatment of HIV-AIDS Infection", Journal of Medicinal Chemistry, 2008, vol. 51, pp. 5843-5855.
The Presidential Green Chemistry Challenge Awards Program—Nomination Package for 2008 Awards, U.S. Environmental Protection Agency, Jun. 2007.
"An Efficient Green Synthesis of Isentress®: A Breakthrough HIV Integrase Inhibitor", Merck's Entry to the Presidential Green Chemistry Challenge Awards Program, Submitted by e-mail Dec. 31, 2007 by Dr. John Leazer.
The Presidential Green Chemistry Challenge Awards Program: Summary of 2008 Award Entries and Recipients, U.S. Environmental Protection Agency, Jun. 2008, p. 47.

*Primary Examiner* — Deepak Rao
(74) *Attorney, Agent, or Firm* — Jeffrey P. Bergman; Sheldon O. Heber

(57) ABSTRACT

Processes for preparing certain N-arylalkyl-1-(alkyl or aralkyl)-2-acylaminoalkyl-5-hydroxy-6-oxo-1,6-dihydropyrimidine-4-carboxamides are disclosed. In one embodiment, the process comprises acylating the free amine in the corresponding N-arylalkyl-1-(alkyl or aralkyl)-2-aminoalkyl-5-ester protected hydroxy-6-oxo-1,6-dihydropyrimidine-4-carboxamide and then deprotecting the 5-hydroxy by base hydrolysis. The hydroxypyrimidinone carboxamide products of the process are HTV integrase inhibitors which are useful for treating HTV infection, treating AIDS, or delaying the onset or progression of AIDS. Certain esterified N-arylalkyl hydroxypyrimidinone carboxamides that can be employed as process intermediates are also disclosed.

(I)

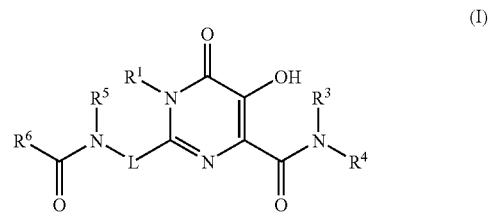

27 Claims, No Drawings

PROCESS FOR PREPARING N-SUBSTITUTED HYDROXYPYRIMIDINONE CARBOXAMIDES

CROSS-REFERENCE TO RELATED APPLICATIONS

This application is the National Stage of International Application No. PCT/US2008/087929, filed on Dec. 22, 2008, which claims the benefit of U.S. Provisional Application No. 61/010,421, filed Jan. 8, 2008, the disclosure of which is incorporated by reference herein in its entirety.

FIELD OF THE INVENTION

The present invention is directed to a process for preparing certain N-arylalkyl hydroxypyrimidinone carboxamides which are useful as HIV integrase inhibitors. The present invention is also directed to certain esterified N-arylalkyl hydroxypyrimidinone carboxamides that can be employed as intermediates in the process of the invention.

BACKGROUND OF THE INVENTION

A class of N-arylalkyl-1-(alkyl or aralkyl)-2-acylaminoalkyl-5-hydroxy-6-oxo-1,6-dihydropyrimidine-4-carboxamides are inhibitors of the HIV integrase enzyme. More particularly, these compounds can inhibit the HIV type 1 (HIV-1) integrase enzyme and the HIV type 2 (HIV-2) integrase enzyme. This class includes the compounds of Formula I as defined and described below. These compounds and pharmaceutically acceptable salts thereof are useful in the treatment or prophylaxis of infection by HIV and in the treatment, prophylaxis, or delay in the onset or progression of AIDS. Representative compounds of this class are described in International Publication No. WO 03/035077 and in corresponding U.S. Pat. No. 7,169,780. Among the compounds disclosed in WO 03/035077 is N-(4-fluorobenzyl)-5-hydroxy-1-methyl-2-(1-methyl-1-{[(5-methyl-1,3,4-oxadiazol-2-yl)carbonyl]amino}ethyl)-6-oxo-1,6-dihydropyrimidine-4-carboxamide, hereinafter referred to as Compound A. The generic name of Compound A is raltegravir, and raltegravir potassium is the active ingredient in ISENTRESS (Merck & Co., Inc.) which is indicated in combination with other antiretroviral agents for the treatment of HIV-1 infection in treatment-experienced adult patients with evidence of viral replication and HIV-1 strains resistant to multiple antiretroviral agents. The structure of Compound A is as follows:

Compound A

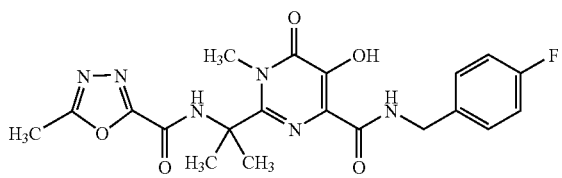

US 2006/0122205 and corresponding WO 2006/060730 disclose a method that can be employed to prepare compounds of the above-described class. The method involves (i) alkylating an alkyl 2-[(protected amino)alkyl]-5-hydroxy-6-oxo-1,6-dihydropyrimidine-4-carboxylate to obtain alkyl 2-[(protected amino)alkyl]-1-alkyl-5-hydroxy-6-oxo-1,6-dihydropyrimidine-4-carboxylate, (ii) coupling the product of step i with an aralkylamine to obtain N-aralkyl 2-[(protected amino)alkyl]-1-alkyl-5-hydroxy-6-oxo-1,6-dihydropyrimidine-4-carboxamide, (iii) deprotecting the 2-aminoalkyl group in the product of step ii to obtain N-aralkyl 2-aminoalkyl-1-alkyl-5-hydroxy-6-oxo-1,6-dihydropyrimidine-4-carboxamide, and (iv) acylating the 2-aminoalkyl group with a suitable acylating agent to obtain a compound of the class. The preparation of Compound A as described in US 2006/0122205 is representative:

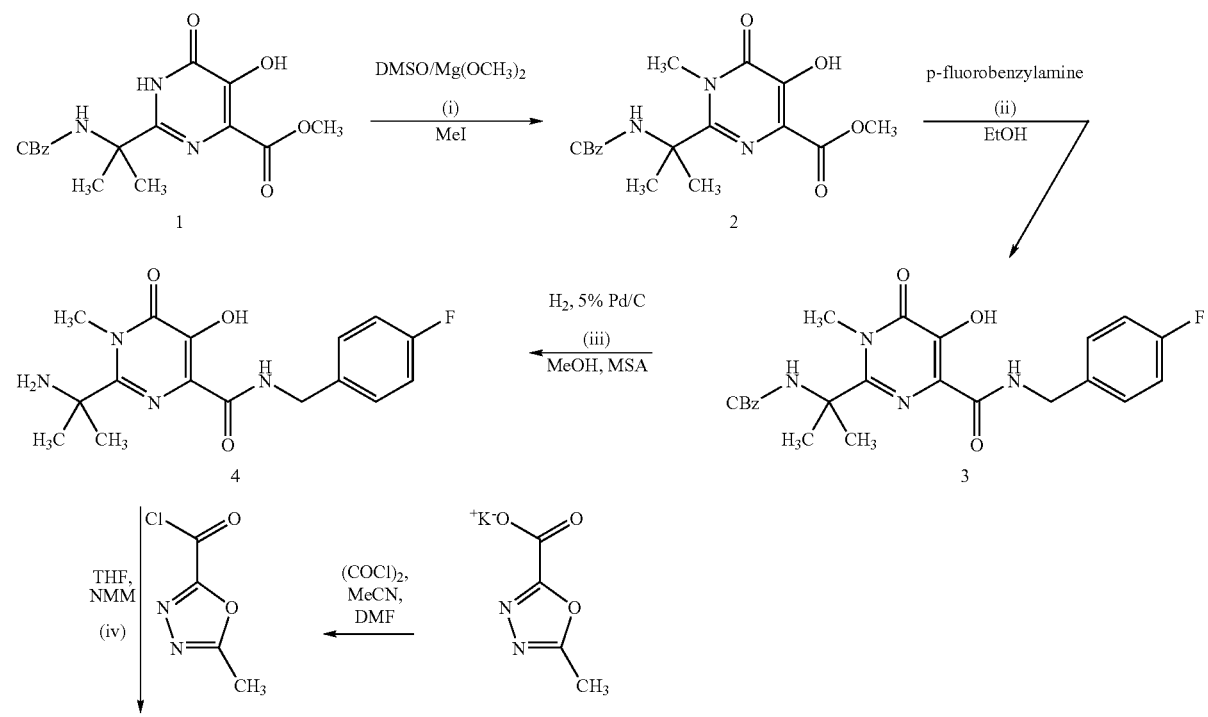

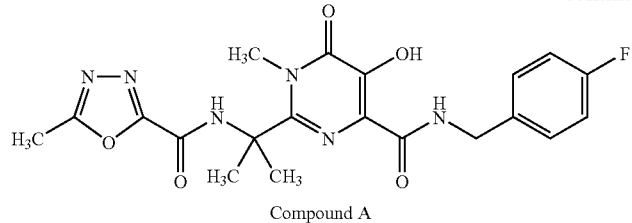
Compound A
WO 03/035077 discloses processes related to the process described in US 2006/0122205 including a preparation of Compound A (see Steps 4, 5, 6, (no step 7), 8 and 9 of Example 18 and Example 19):
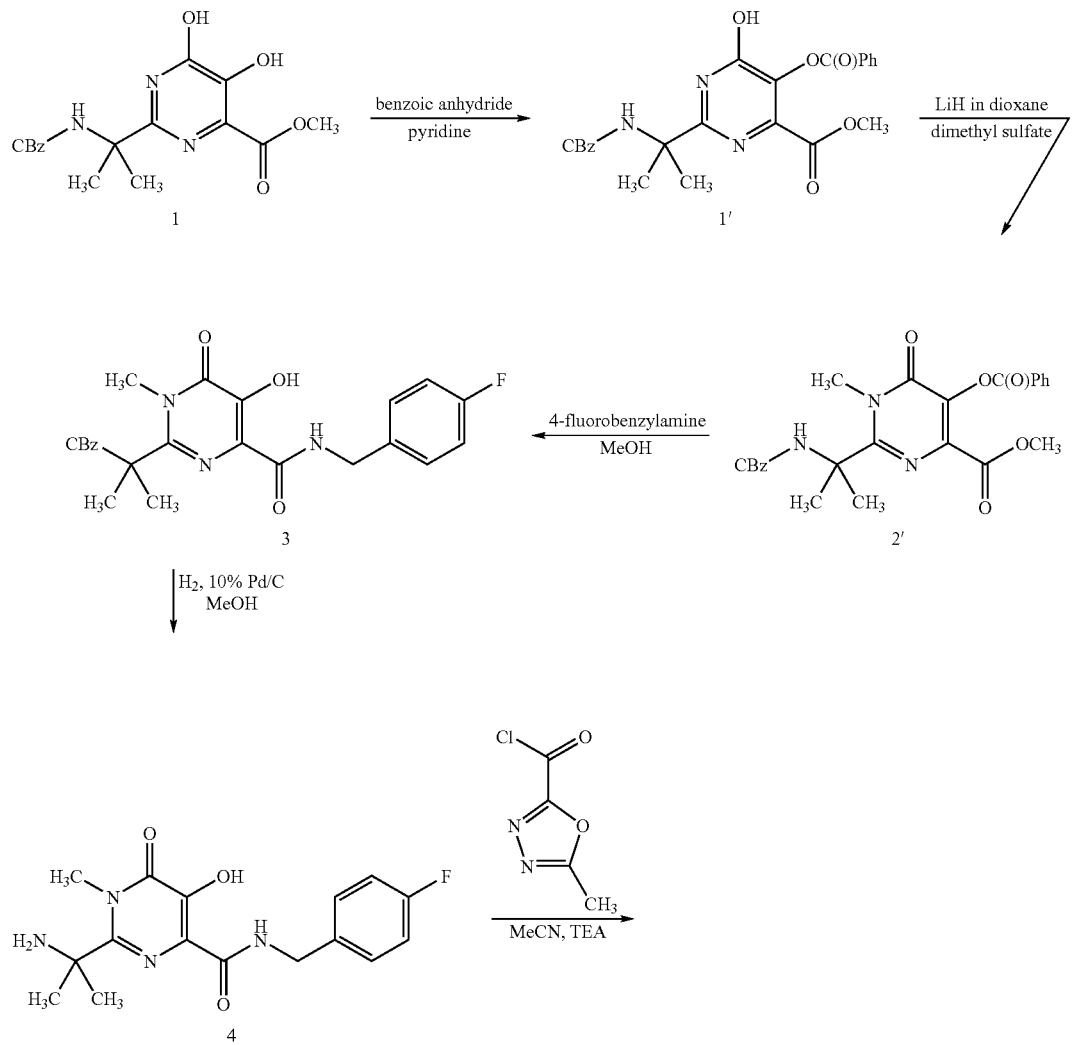
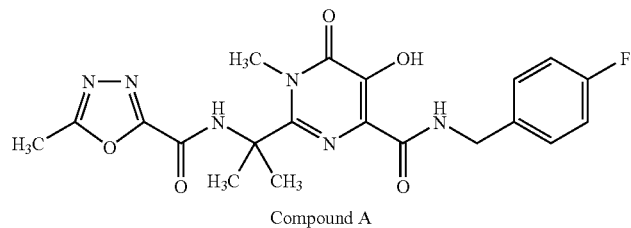
Compound A The routes described above are practical routes for the preparation of Compound A and related hydroxypyrimidinone carboxamides. In particular, the route described US 2006/0122205 can be employed for the large-scale production of Compound A. Nonetheless, there is always a need for alternative preparative routes which, for example, use reagents that are less expensive and/or easier to handle, consume smaller amounts of reagents, provide a higher yield of product, involve fewer steps, have smaller and/or more eco-friendly waste products, and/or provide a product of higher purity.

SUMMARY OF THE INVENTION

The present invention is directed to a process for preparing certain N-arylalkyl-1-(alkyl or aralkyl)-2-acylaminoalkyl-5-hydroxy-6-oxo-1,6-dihydropyrimidine-4-carboxamides which are useful as HIV integrase inhibitors. More particularly, the present invention includes a process (alternatively referred to herein as Process P) for preparing a compound of Formula I:

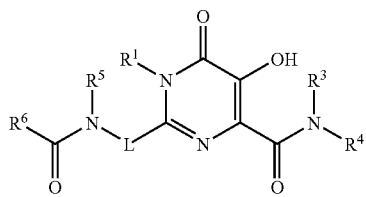

(I)

which comprises:
(A) contacting a compound of Formula II:

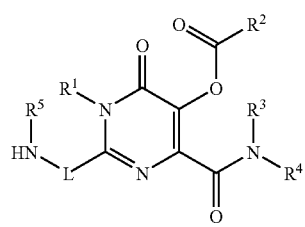

(II)

with an acylating agent of Formula III:

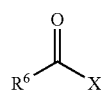

(III)

in organic solvent A and in the presence of base to obtain an acylated amine compound of Formula IV:

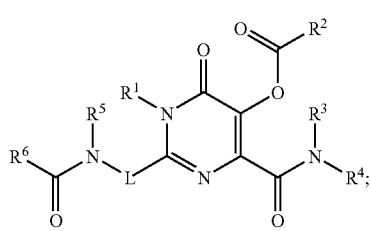

(IV)

and
(B) contacting the compound of Formula IV with an aqueous base in organic solvent B to obtain the compound of Formula I; wherein:

X is halogen or $OC(O)R^6$;

$R^1$ is $C_{1-6}$ alkyl or $C_{1-6}$ alkyl substituted with AryA;

$R^2$ is $C_{1-8}$ alkyl or AryB;

$R^3$ is H or $C_{1-6}$ alkyl;

$R^4$ is $C_{1-6}$ alkyl substituted with AryC;

AryC is phenyl or naphthyl, wherein the phenyl or naphthyl is optionally substituted with from 1 to 4 substituents each of which is independently:

(1) $C_{1-6}$ alkyl,
(2) $C_{3-6}$ cycloalkyl,
(3) $C_{1-6}$ haloalkyl,
(4) $O-C_{1-6}$ alkyl,
(5) $O-C_{1-6}$ haloalkyl,
(6) $O-C_{3-6}$ cycloalkyl,
(7) $S-C_{1-6}$ alkyl,
(8) $S-C_{1-6}$ haloalkyl,
(9) $S-C_{3-6}$ cycloalkyl,
(10) halo,
(11) CN,
(12) $NO_2$,
(13) $N(H)R^E$,
(14) $N(-C_{1-6}$ alkyl$)_2$,
(15) CH(O),
(16) $C(O)-C_{1-6}$ alkyl,
(17) $C(O)O-C_{1-6}$ alkyl,
(18) $C(O)NH_2$,
(19) $C(O)N(H)-C_{1-6}$ alkyl,
(20) $C(O)N(-C_{1-6}$ alkyl$)_2$,
(21) $C_{1-6}$ alkyl substituted with:
  (a) $O-C_{1-6}$ alkyl,
  (b) $O-C_{1-6}$ haloalkyl,
  (c) $O-C_{3-6}$ cycloalkyl,
  (d) $S-C_{1-6}$ alkyl,
  (e) CN,
  (f) $NO_2$,
  (g) $N(H)R^E$,
  (h) $N(-C_{1-6}$ alkyl$)_2$,
  (i) CH(O),
  (j) $C(O)-C_{1-6}$ alkyl,
  (k) $C(O)O-C_{1-6}$ alkyl,
  (l) $C(O)NH_2$,
  (m) $C(O)N(H)-C_{1-6}$ alkyl, or
  (n) $C(O)N(-C_{1-6}$ alkyl$)_2$, or
(22) AryQ, with the proviso that no more than one of the optional substituents is AryQ;

AryA independently has the same definition as AryC;
AryB independently has the same definition as AryC;

L is $C_{1-6}$ alkylene;
$R^5$ is H or $C_{1-6}$ alkyl;
$R^6$ is:
  (1) HetP,
  (2) $C_{1-6}$ alkyl substituted with HetP,
  (3) C(O)—$C_{1-6}$ alkylene-HetP,
  (4) C(O)-HetP,
  (5) CycQ,
  (6) O-CycQ,
  (7) C(O)-CycQ,
  (8) C(O)O-CycQ,
  (9) AryQ,
  (10) O-AryQ,
  (11) C(O)-AryQ,
  (12) C(O)O-AryQ,
  (13) HetQ,
  (14) O-HetQ,
  (15) C(O)-HetQ, or
  (16) C(O)O-HetQ;
$R^E$ is a branched $C_{3-6}$ alkyl;
HetP is a 4- to 7-membered saturated or mono-unsaturated heterocyclic ring containing 1 N atom through which the ring is attached to the rest of the compound and optionally containing an additional heteroatom wherein the additional heteroatom is selected from N, O, and S; wherein the optional S in the ring is optionally in the form of S(O) or $S(O)_2$ and the optional N in the ring is substituted with $C_{1-6}$ alkyl, C(O)—$C_{1-6}$ alkyl, or C(O)O—$C_{1-6}$ alkyl when the ring is saturated and is part of the ring double bond when the ring is mono-unsaturated;
CycQ is a $C_{3-7}$ cycloalkyl which is optionally substituted with from 1 to 3 substituents each of which is independently halogen, $C_{1-6}$ alkyl, $C_{1-6}$ haloalkyl, O—$C_{1-6}$ alkyl, O—$C_{1-6}$ haloalkyl, oxo, $N(C_{1-6}$ alkyl$)_2$, $C(O)N(C_{1-6}$ alkyl$)_2$, C(O)—$C_{1-6}$ alkyl, or C(O)O—$C_{1-6}$ alkyl;
each AryQ is independently phenyl which is optionally substituted with from 1 to 4 substituents each of which is independently halogen, CN, $NO_2$, $C_{1-6}$ alkyl, $C_{1-6}$ haloalkyl, O—$C_{1-6}$ alkyl, O—$C_{1-6}$ haloalkyl, S—$C_{1-6}$ alkyl, $N(C_{1-6}$ alkyl$)_2$, $C(O)N(C_{1-6}$ alkyl$)_2$, C(O)—$C_{1-6}$ alkyl, or C(O)O—$C_{1-6}$ alkyl; and
HetQ is a heteroaryl which is a 5- or 6-membered heteroaromatic ring containing from 1 to 4 heteroatoms independently selected from N, O and S, to which is optionally fused a benzene ring; wherein the heteroaryl is optionally substituted with from 1 to 4 substituents each of which is independently halogen, CN, $NO_2$, $C_{1-6}$ alkyl, $C_{1-6}$ haloalkyl, O—$C_{1-6}$ alkyl, O—$C_{1-6}$ haloalkyl, S—$C_{1-6}$ alkyl, N(—$C_{1-6}$ alkyl$)_2$, C(O)N(—$C_{1-6}$ alkyl$)_2$, C(O)—$C_{1-6}$ alkyl, or C(O)O—$C_{1-6}$ alkyl.

A compound of Formula I is alternatively referred to herein more simply as Compound I. Similarly, the compound of Formula II is alternatively referred to as Compound II or free amine II, the acylating agent of Formula III is alternatively referred to as Compound III or acylating agent III, and the compound of Formula IV is alternatively referred to as Compound IV or acylated amine IV. Analogous nomenclature is employed for other compounds described below.

Unlike the processes for making N-arylalkyl-1-(alkyl or aralkyl)-2-acylaminoalkyl-5-hydroxy-6-oxo-1,6-dihydropyrimidine-4-carboxamides described in US 2006/0122205 (alternatively referred to herein as U.S. '205) and in WO 03/035077 (alternatively referred to herein as WO '077), the process of the present invention employs a protected hydroxypyrimidinone substrate; i.e., the 5-hydroxy group in the compound of Formula II is esterified to OC(O)—$R^2$. The use of the hydroxy protected substrate in the present invention significantly reduces the amount of acylating agent (i.e, $R^6$—C(O)X) required for complete conversion in comparison to the US 2006/0122205 and in WO 03/035077 processes (i.e., the "other two processes"). More particularly, the process of the invention requires one equivalent of acylating agent per equivalent of substrate II for complete conversion, whereas the other two processes require 2 equivalents. Typically $R^2$ and $R^6$ are not the same group and the acylating agent $R^6$—C(O)X is comparatively expensive, and thus the process of the present invention can generate significant cost savings over the other two processes, particularly when the process is employed for the large scale production of Compound I.

Substrates of Formula II in which Y=H are often crystalline and non-hygroscopic, whereas the corresponding dihydroxypyrimidine substrates employed in the other two processes are often non-crystalline and hygroscopic and thus more difficult to isolate and handle.

Other embodiments, aspects and features of the present invention are either further described in or will be apparent from the ensuing description, examples, and appended claims.

DETAILED DESCRIPTION OF THE INVENTION

The present invention is directed to a process for preparing a N-arylalkyl-1-(alkyl or aralkyl)-2-acylaminoalkyl-5-hydroxy-6-oxo-1,6-dihydropyrimidine-4-carboxamide by first acylating the free amine in the corresponding N-arylalkyl-1-(alkyl or aralkyl)-2-aminoalkyl-5-ester protected hydroxy-6-oxo-1,6-dihydropyrimidine-4-carboxamide and then deprotecting the 5-hydroxy by base hydrolysis. The present invention includes the process comprising Steps A and B as set forth above in the Summary of the Invention (i.e., Process P).

A first embodiment of the present invention (alternatively referred to herein as Embodiment E1) is Process P, wherein $R^1$ is $C_{1-4}$ alkyl or $CH_2$-AryA; and all other variables are as originally defined (i.e., as defined in the Summary of the Invention). In an aspect of this embodiment, $R^1$ is $C_{1-4}$ alkyl or $CH_2$-AryA wherein AryA is phenyl which is optionally substituted with from 1 to 4 substituents each of which is independently Cl, Br, F, CN, $NO_2$, $C_{1-4}$ alkyl, $C_{1-4}$ fluoroalkyl, O—$C_{1-4}$ alkyl, O—$C_{1-4}$ fluoroalkyl, S—$C_{1-4}$ alkyl, CH(O), C(O)—$C_{1-4}$ alkyl, $C(O)_{1-4}$ alkyl, $C(O)NH_2$, C(O)N(H)—$C_{1-4}$ alkyl, or C(O)N(—$C_{1-4}$ alkyl$)_2$.

A second embodiment of the present invention (Embodiment E2) is Process P, wherein $R^1$ is $CH_3$ or $CH_2$-AryA wherein AryA is phenyl which is optionally substituted with from 1 to 3 substituents each of which is independently Cl, Br, F, CN, $C_{1-4}$ alkyl, O—$C_{1-4}$ alkyl, $CF_3$, or $OCF_3$; and all other variables are as originally defined.

A third embodiment of the present invention (Embodiment E3) is Process P, wherein $R^1$ is $CH_3$ or benzyl; and all other variables are as originally defined.

A fourth embodiment of the present invention (Embodiment E4) is Process P, wherein $R^1$ is $CH_3$; and all other variables are as originally defined.

A fifth embodiment of the present invention (Embodiment E5) is Process P, wherein $R^2$ is a branched $C_{3-8}$ alkyl or AryB; and all other variables are as originally defined or as defined in any one of the preceding embodiments. In an aspect of this embodiment, AryB is phenyl which is optionally substituted with from 1 to 4 substituents each of which is independently Cl, Br, F, CN, $NO_2$, $C_{1-4}$ alkyl, $C_{1-4}$ fluoroalkyl, O—$C_{1-4}$ alkyl, O—$C_{1-4}$ fluoroalkyl, S—$C_{1-4}$ alkyl, CH(O), C(O)—$C_{1-4}$ alkyl, C(O)O—$C_{1-4}$ alkyl, $C(O)NH_2$, C(O)N(H)—$C_{1-4}$ alkyl, or C(O)N(—$C_{1-4}$ alkyl$)_2$.

A sixth embodiment of the present invention (Embodiment E6) is Process P, wherein $R^2$ is branched $C_{3-6}$ alkyl or AryB wherein AryB is phenyl which is optionally substituted with from 1 to 3 substituents each of which is independently Cl, Br, F, CN, $C_{1-4}$ alkyl, O—$C_{1-4}$ alkyl, $CF_3$, or $OCF_3$; and all other variables are as originally defined or as defined in any one of the preceding embodiments.

A seventh embodiment of the present invention (Embodiment E7) is Process P, wherein $R^2$ is branched $C_{3-6}$ alkyl or phenyl; and all other variables are as originally defined or as defined in any one of the preceding embodiments.

An eighth embodiment of the present invention (Embodiment E8) is Process P, wherein $R^2$ is branched $C_{3-6}$ alkyl; and all other variables are as originally defined or as defined in any one of the preceding embodiments.

A ninth embodiment of the present invention (Embodiment E9) is Process P, wherein $R^2$ is t-butyl; and all other variables are as originally defined or as defined in any one of the preceding embodiments.

A tenth embodiment of the present invention (Embodiment E10) is Process P, wherein $R^3$ is H or $C_{1-4}$ alkyl; and all other variables are as originally defined or as defined in any one of the preceding embodiments.

An eleventh embodiment of the present invention (Embodiment E11) is Process P, wherein $R^3$ is H or $CH_3$; and all other variables are as originally defined or as defined in any one of the preceding embodiments.

A twelfth embodiment of the present invention (Embodiment E12) is Process P, wherein $R^3$ is H; and all other variables are as originally defined or as defined in any one of the preceding embodiments.

A thirteenth embodiment of the present invention (Embodiment E13) is Process P, wherein $R^4$ is $C_{1-4}$ alkyl substituted with AryC; and all other variables are as originally defined or as defined in any one of the preceding embodiments.

A fourteenth embodiment of the present invention (Embodiment E14) is Process P, wherein $R^4$ is $CH_2$-AryC, $CH(CH_3)$-AryC, $C(CH_3)_2$-AryC or $CH_2CH_2$-AryC; and all other variables are as originally defined or as defined in any one of the preceding embodiments.

A fifteenth embodiment of the present invention (Embodiment E15) is Process P, wherein $R^4$ is $CH_2$-AryC; and all other variables are as originally defined or as defined in any one of the preceding embodiments. In an aspect of this embodiment, $R^4$ is

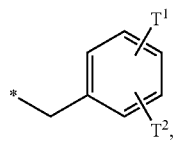

wherein $T^1$ and $T^2$ are each independently H, Cl, Br, F, CN, $C_{1-4}$ alkyl, $C_{1-4}$ fluoroalkyl, O—$C_{1-4}$ alkyl, O—$C_{1-4}$ fluoroalkyl, $N(CH_3)_2$, $C(O)CH_3$, or $CO_2CH_3$. In another aspect of this embodiment, $R^4$ is 4-fluorobenzyl.

A sixteenth embodiment of the present invention (Embodiment E16) is Process P, wherein AryC is phenyl, wherein the phenyl is optionally substituted with from 1 to 3 substituents each of which is independently:

(1) $C_{1-4}$ alkyl,
(2) $C_{3-6}$ cycloalkyl,
(3) $C_{1-4}$ fluoroalkyl,
(4) O—$C_{1-4}$ alkyl,
(5) O—$C_{1-4}$ fluoroalkyl,
(6) O—$C_{3-6}$ cycloalkyl,
(7) halo,
(8) CN,
(9) N(H)-isopropyl,
(10) N(H)-t-butyl,
(11) N(—$C_{1-4}$ alkyl)$_2$,
(12) CH(O),
(13) C(O)—$C_{1-4}$ alkyl,
(14) C(O)O—$C_{1-4}$ alkyl,
(15) $C(O)NH_2$,
(16) C(O)N(H)—$C_{1-4}$ alkyl,
(17) C(O)N(—$C_{1-4}$ alkyl)$_2$,
(18) $C_{1-4}$ alkyl substituted with:
  (a) O—$C_{1-4}$ alkyl,
  (b) O—$C_{1-4}$ fluoroalkyl,
  (c) O—$C_{3-6}$ cycloalkyl,
  (d) CN,
  (e) $NO_2$,
  (f) N(H)-isopropyl,
  (g) N(H)-t-butyl,
  (h) N(—$C_{1-4}$ alkyl)$_2$,
  (i) CH(O),
  (j) C(O)—$C_{1-4}$ alkyl,
  (k) C(O)O—$C_{1-4}$ alkyl,
  (l) $C(O)NH_2$,
  (m) C(O)N(H)—$C_{1-6}$ alkyl, or
  (n) C(O)N(—$C_{1-6}$ alkyl)$_2$, or
(19) phenyl, with the proviso that no more than one of the optional substituents is phenyl;

and all other variables are as originally defined or as defined in any one of the preceding embodiments.

A seventeenth embodiment of the present invention (Embodiment E17) is Process P, wherein AryC is phenyl which is optionally substituted with from 1 to 3 substituents each of which is independently Cl, Br, F, CN, $C_{1-4}$ alkyl, $C_{1-4}$ fluoroalkyl, O—$C_{1-4}$ alkyl, O—$C_{1-4}$ fluoroalkyl, $N(CH_3)_2$, C(O)$CH_3$, or $CO_2CH_3$; and all other variables are as originally defined or as defined in any one of the preceding embodiments.

An eighteenth embodiment of the present invention (Embodiment E18) is Process P, wherein AryC is

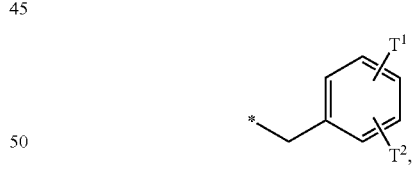

wherein $T^1$ and $T^2$ are each independently H, Cl, Br, F, CN, $C_{1-4}$ alkyl, $C_{1-4}$ fluoroalkyl, O—$C_{1-4}$ alkyl, O—$C_{1-4}$ fluoroalkyl, $N(CH_3)_2$, $C(O)CH_3$, or $CO_2CH_3$; and all other variables are as originally defined or as defined in any one of the preceding embodiments.

A nineteenth embodiment of the present invention (Embodiment E19) is Process P, wherein AryC is phenyl which is optionally substituted with from 1 to 3 substituents each of which is independently Cl, Br, F, CN, $CH_3$, $CF_3$, $OCH_3$, $OCF_3$, $N(CH_3)_2$, $C(O)CH_3$, or $CO_2CH_3$; and all other variables are as originally defined or as defined in any one of the preceding embodiments.

A twentieth embodiment of the present invention (Embodiment E20) is Process P, wherein AryC is phenyl which is optionally substituted with from 1 to 3 substituents each of which is independently Cl, Br, F, $CH_3$, or $CF_3$; and all other variables are as originally defined or as defined in any one of the preceding embodiments.

A twenty-first embodiment of the present invention (Embodiment E21) is Process P, wherein AryC is phenyl which is optionally substituted with 1 or 2 substituents each of which is independently Cl, Br, F, or $CH_3$; and all other variables are as originally defined or as defined in any one of the preceding embodiments.

A twenty-second embodiment of the present invention (Embodiment E22) is Process P, wherein AryC is 4-fluorophenyl; and all other variables are as originally defined or as defined in any one of the preceding embodiments.

A twenty-third embodiment of the present invention (Embodiment E23) is Process P, wherein L is $C_{1-3}$ alkylene; and all other variables are as originally defined or as defined in any one of the preceding embodiments.

A twenty-fourth embodiment of the present invention (Embodiment E24) is Process P, wherein L is $CH_2$, $CH(CH_3)$, $C(CH_3)_2$, or $CH_2CH_2$; and all other variables are as originally defined or as defined in any one of the preceding embodiments.

A twenty-fifth embodiment of the present invention (Embodiment E25) is Process P, wherein L is $CH_2$, $CH(CH_3)$, or $C(CH_3)_2$; and all other variables are as originally defined or as defined in any one of the preceding embodiments.

A twenty-sixth embodiment of the present invention (Embodiment E26) is Process P, wherein L is $C(CH_3)_2$; and all other variables are as originally defined or as defined in any one of the preceding embodiments.

A twenty-seventh embodiment of the present invention (Embodiment E27) is Process P, wherein $R^5$ is H or $C_{1-4}$ alkyl; and all other variables are as originally defined or as defined in any one of the preceding embodiments.

A twenty-eighth embodiment of the present invention (Embodiment E28) is Process P, wherein $R^5$ is H or $CH_3$; and all other variables are as originally defined or as defined in any one of the preceding embodiments.

A twenty-ninth embodiment of the present invention (Embodiment E29) is Process P, wherein $R^5$ is H; and all other variables are as originally defined or as defined in any one of the preceding embodiments.

A thirtieth embodiment of the present invention (Embodiment E30) is Process P, wherein $R^6$ is: (1) $C_{1-6}$ alkyl substituted with HetP, (2) HetP, (3) AryQ, or (4) HetQ; and all other variables are as originally defined or as defined in any one of the preceding embodiments.

A thirty-first embodiment of the present invention (Embodiment E31) is Process P, wherein $R^6$ is AryQ or HetQ; and all other variables are as originally defined or as defined in any one of the preceding embodiments.

A thirty-second embodiment of the present invention (Embodiment E32) is Process P, wherein $R^6$ is AryQ; and all other variables are as originally defined or as defined in any one of the preceding embodiments.

A thirty-third embodiment of the present invention (Embodiment E33) is Process P, wherein $R^6$ is HetQ; and all other variables are as originally defined or as defined in any one of the preceding embodiments.

A thirty-fourth embodiment of the present invention (Embodiment E34) is Process P, wherein $R^6$ is 5-methyl-1,3,4-oxadiazol-2-yl; and all other variables are as originally defined or as defined in any one of the preceding embodiments.

A thirty-fifth embodiment of the present invention (Embodiment E35) is Process P, wherein X is halogen; and all other variables are as originally defined or as defined in any one of the preceding embodiments.

A thirty-sixth embodiment of the present invention (Embodiment E36) is Process P, wherein X is Cl or Br; and all other variables are as originally defined or as defined in any one of the preceding embodiments.

A thirty-seventh embodiment of the present invention (Embodiment E37) is Process P, wherein X is Cl; and all other variables are as originally defined or as defined in any one of the preceding embodiments.

A thirty-eighth embodiment of the present invention (Embodiment E38) is Process P, wherein HetP is a saturated heterocyclic ring selected from the group consisting of:

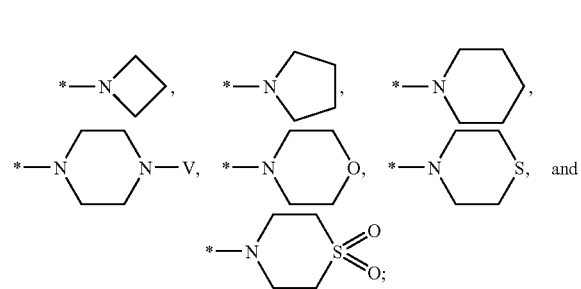

wherein the asterisk (*) denotes the point of attachment to the rest of the compound and V is $C_{1-4}$ alkyl, C(O)—$C_{1-4}$ alkyl, or C(O)O—$C_{1-4}$ alkyl; and all other variables are as originally defined or as defined in any one of the preceding embodiments.

A thirty-ninth embodiment of the present invention (Embodiment E39) is Process P, wherein HetP is a saturated heterocyclic ring selected from the group consisting of:

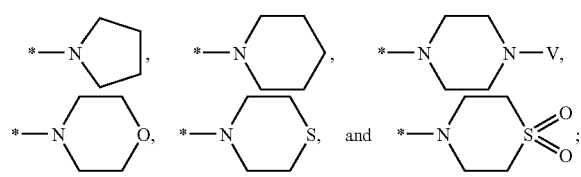

wherein the asterisk (*) denotes the point of attachment to the rest of the compound and V is $CH_3$, $C(O)CH_3$, or $C(O)OCH_3$; and all other variables are as originally defined or as defined in any one of the preceding embodiments.

A fortieth embodiment of the present invention (Embodiment E40) is Process P, wherein $R^E$ is isopropyl, t-butyl, sec-butyl, isobutyl, isopentyl (i.e., 3-methyl-1-butyl), 2-methyl-1-butyl, diethylmethyl, 2-pentyl, or neopentyl; and all other variables are as originally defined or as defined in any one of the preceding embodiments.

A forty-first embodiment of the present invention (Embodiment E41) is Process P, wherein $R^E$ is isopropyl or t-butyl; and all other variables are as originally defined or as defined in any one of the preceding embodiments.

A forty-second embodiment of the present invention (Embodiment E42) is Process P, wherein CycQ is a $C_{5-7}$ cycloalkyl, wherein the cycloalkyl is optionally substituted with from 1 to 3 substituents each of which is independently halogen, $C_{1-4}$ alkyl, $C_{1-4}$ haloalkyl, O—$C_{1-4}$ alkyl, O—$C_{1-4}$ haloalkyl, oxo, N(—$C_{1-4}$ alkyl)$_2$, C(O)N(—$C_{1-4}$ alkyl)$_2$, C(O)—$C_{1-4}$ alkyl, or C(O)O—$C_{1-4}$ alkyl; and all other variables are as originally defined or as defined in any one of the preceding embodiments.

A forty-third embodiment of the present invention (Embodiment E43) is Process P, wherein CycQ is a $C_{5-7}$ cycloalkyl, wherein the cycloalkyl is optionally substituted with from 1 to 3 substituents each of which is independently Cl, Br, F, $CH_3$, $CF_3$, $OCH_3$, $OCF_3$, oxo, $N(CH_3)_2$, $C(O)N$ $(CH_3)_2$, $C(O)CH_3$, or $CO_2CH_3$; and all other variables are as originally defined or as defined in any one of the preceding embodiments.

A forty-fourth embodiment of the present invention (Embodiment E44) is Process P, wherein CycQ is unsubstituted $C_{5-7}$ cycloalkyl; and all other variables are as originally defined or as defined in any one of the preceding embodiments.

A forty-fifth embodiment of the present invention (Embodiment E45) is Process P, wherein AryQ is phenyl which is optionally substituted with from 1 to 3 substituents each of which is independently halogen, CN, $NO_2$, $C_{1-4}$ alkyl, $C_{1-4}$ haloalkyl, O—$C_{1-4}$ alkyl, O—$C_{1-4}$ haloalkyl, S—$C_{1-4}$ alkyl, N(—$C_{1-4}$ alkyl)$_2$, C(O)N(—$C_{1-4}$ alkyl)$_2$, C(O)—$C_{1-4}$ alkyl, or C(O)O—$C_{1-4}$ alkyl; and all other variables are as originally defined or as defined in any one of the preceding embodiments.

A forty-sixth embodiment of the present invention (Embodiment E46) is Process P, wherein AryQ is phenyl which is optionally substituted with from 1 to 3 substituents each of which is independently Cl, Br, F, $CH_3$, $CF_3$, $OCH_3$, $OCF_3$, $SCH_3$, $N(CH_3)_2$, $C(O)N(CH_3)_2$, $C(O)CH_3$, or $CO_2CH_3$; and all other variables are as originally defined or as defined in any one of the preceding embodiments.

A forty-seventh embodiment of the present invention (Embodiment E47) is Process P, wherein AryQ is phenyl which is optionally substituted with from 1 to 3 substituents each of which is independently Cl, Br, F, $CH_3$, $CF_3$, $OCH_3$, $OCF_3$; and all other variables are as originally defined or as defined in any one of the preceding embodiments.

A forty-eighth embodiment of the present invention (Embodiment E48) is Process P, wherein HetQ is a heteroaromatic ring selected from the group consisting of furanyl, thienyl, pyrrolyl, pyrazolyl, imidazolyl, triazolyl, tetrazolyl, oxazolyl, isoxazolyl, thiazolyl, isothiazolyl, oxadiazolyl, thiadiazolyl, pyridyl, pyrimidinyl, pyrazinyl, and pyridazinyl; wherein the heteroaromatic ring is optionally substituted with from 1 to 3 substituents each of which is independently halogen, CN, $NO_2$, $C_{1-4}$ alkyl, $C_{1-4}$ haloalkyl, O—$C_{1-4}$ alkyl, O—$C_{1-4}$ haloalkyl, S—$C_{1-4}$ alkyl, N(—$C_{1-4}$ alkyl)$_2$, C(O)N (—$C_{1-4}$ alkyl)$_2$, C(O)—$C_{1-4}$ alkyl, or C(O)O—$C_{1-4}$ alkyl; and all other variables are as originally defined or as defined in any one of the preceding embodiments.

A forty-ninth embodiment of the present invention (Embodiment E49) is Process P, wherein HetQ is a heteroaromatic ring selected from the group consisting of furanyl, thienyl, pyrrolyl, pyrazolyl, imidazolyl, triazolyl, tetrazolyl, oxazolyl, isoxazolyl, thiazolyl, isothiazolyl, oxadiazolyl, thiadiazolyl, pyridyl, pyrimidinyl, pyrazinyl, and pyridazinyl; wherein the heteroaromatic ring is optionally substituted with from 1 to 3 substituents each of which is independently Cl, Br, F, $CH_3$, $CF_3$, $OCH_3$, $OCF_3$, $SCH_3$, $N(CH_3)_2$, $C(O)N$ $(CH_3)_2$, $C(O)CH_3$, or $CO_2CH_3$; and all other variables are as originally defined or as defined in any one of the preceding embodiments.

A forty-ninth embodiment of the present invention (Embodiment E49) is Process P, wherein HetQ is a heteroaromatic ring selected from the group consisting of oxazolyl, isoxazolyl, thiazolyl, isothiazolyl, oxadiazolyl, or thiadiazolyl, wherein the heteroaromatic ring is optionally substituted with 1 or 2 substituents each of which is independently Cl, Br, F, $CH_3$, $CF_3$, $OCH_3$, $OCF_3$; and all other variables are as originally defined or as defined in any one of the preceding embodiments.

A fiftieth embodiment of the present invention (Embodiment E50) is Process P, wherein HetQ is

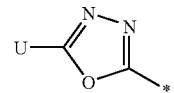

wherein U is H or $CH_3$, and all other variables are as originally defined or as defined in any one of the preceding embodiments. In an aspect of this embodiment, HetQ is 5-methyl-1,3,4-oxadiazol-2-yl.

The original definitions of $R^2$ and $R^6$ and certain of the definitions of $R^2$ and $R^6$ set forth in the foregoing embodiments overlap, such that it is possible for $R^2$ and $R^6$ to be the same group. On the other hand, $R^2$ and $R^6$ are typically not the same in the process of the invention and thus the following embodiment: A fifty-first embodiment of the present invention (Embodiment E51) is Process P wherein all of the variables are as originally defined, with the proviso that when $R^2$ is AryB and $R^6$ is AryQ, then AryB and AryQ are not the same. Sub-embodiments of this embodiment include all embodiments of Process P incorporating overlapping definitions of $R^2$ and $R^6$ (e.g., an embodiment of Process P in which $R^2$ is as defined in Embodiment E6 and $R^6$ is as defined in Embodiment E30), with the proviso that when $R^2$ is AryB and $R^6$ is AryQ, then AryB and AryQ are not the same.

As used herein, the term "alkyl" refers to a monovalent straight or branched chain, saturated aliphatic hydrocarbon radical having a number of carbon atoms in the specified range. Thus, for example, "$C_{1-8}$ alkyl" (or "$C_1$-$C_8$ alkyl") refers to any of the octyl, heptyl, hexyl and pentyl alkyl isomers as well as n-, iso-, sec- and t-butyl, n- and iso-propyl, ethyl and methyl. As another example, "$C_{1-6}$ alkyl" (or "$C_1$-$C_6$ alkyl") refers to any of the hexyl and pentyl alkyl isomers as well as n-, iso-, see- and t-butyl, n- and iso-propyl, ethyl and methyl. As another example, "$C_{1-4}$ alkyl" refers to n-, iso-, see- and t-butyl, n- and isopropyl, ethyl and methyl. As another example, "$C_{1-3}$ alkyl" refers to n-propyl, isopropyl, ethyl and methyl.

The term "alkylene" refers to any divalent linear or branched chain aliphatic hydrocarbon radical having a number of carbon atoms in the specified range. Thus, for example, "—$C_{1-6}$ alkylene-" refers to any of the $C_1$ to $C_6$ linear or branched alkylenes, and "—$C_{1-4}$ alkylene-" refers to any of the $C_1$ to $C_4$ linear or branched alkylenes. A class of alkylenes of interest with respect to the invention is —$(CH_2)_{1-6}$—, and sub-classes of particular interest include —$(CH_2)_{1-4}$—, —$(CH_2)_{2-4}$—, —$(CH_2)_{1-3}$—, —$(CH_2)_{2-3}$—, —$(CH_2)_{1-2}$—, and —$CH_2$—. Another sub-class of interest is an alkylene selected from the group consisting of —$CH_2$—, —CH($CH_3$)—, —C($CH_3$)$_2$— and $CH_2$—$CH_2$—. Another sub-class of interest is an alkylene selected from the group consisting of —$CH_2$—, —CH($CH_3$)— and —C($CH_3$)$_2$—.

The term "halogen" (or "halo") refers to fluorine, chlorine, bromine and iodine (alternatively referred to as fluoro, chloro, bromo, and iodo).

The term "haloalkyl" refers to an alkyl group as defined above in which one or more of the hydrogen atoms have been replaced with a halogen (i.e., F, Cl, Br and/or I). Thus, for example, "$C_{1-6}$ haloalkyl" (or "$C_1$-$C_6$ haloalkyl") refers to a $C_1$ to $C_6$ linear or branched alkyl group as defined above with one or more halogen substituents. The term "fluoroalkyl" has an analogous meaning except that the halogen substituents are restricted to fluoro. Suitable fluoroalkyls include the series $(CH_2)_{0-4}CF_3$ (i.e., trifluoromethyl, 2,2,2-trifluoroethyl, 3,3,3-trifluoro-n-propyl, etc.). A fluoroalkyl of particular interest is $CF_3$.

The term "cycloalkyl" refers to any monovalent monocyclic ring of an alkane having a number of carbon atoms in the specified range. Thus, for example, "$C_{3-7}$ cycloalkyl" (or "$C_3$-$C_7$ cycloalkyl") refers to cyclopropyl, cyclobutyl, cyclopentyl, cyclohexyl, and cycloheptyl and "$C_{3-6}$ cycloalkyl" refers to cyclopropyl, cyclobutyl, cyclopentyl, and cyclohexyl.

The term "C(O)" refers to carbonyl. The terms "$S(O)_2$" and "$SO_2$" each refer to sulfonyl. The term "S(O)" refers to sulfonyl.

An asterisk ("*") as the end of an open bond in a chemical group denotes the point of attachment of the group to the rest of the compound.

The term "aryl" refers to phenyl and naphthyl. The aryl of particular interest is phenyl.

The term "aralkyl" refers to an alkyl group as defined above substituted with an aryl group as defined above. An aralkyl of particular interest is benzyl. A substituted aralkyl group of particular interest is 4-fluorobenzyl.

The term "heteroaryl" refers to a 5- or 6-membered heteroaromatic ring containing from 1 to 4 heteroatoms independently selected from N, O and S, to which is optionally fused a benzene ring. The term "heteroaryl" includes, for example, pyridyl (also referred to as pyridinyl), pyrrolyl, pyrazinyl, pyrimidinyl, pyridazinyl, triazinyl, thienyl, furanyl, imidazolyl, pyrazolyl, triazolyl, tetrazolyl, oxazolyl, isooxazolyl, oxadiazolyl, oxatriazolyl, thiazolyl, isothiazolyl, thiadiazolyl, quinolinyl, isoquinolinyl, quinazolinyl, benzothiophenyl, benzofuranyl, and indolyl.

Unless expressly stated to the contrary in a particular context, any of the various cyclic rings and ring systems described herein may be attached to the rest of the compound of which they are a part at any ring atom (i.e., any carbon atom or any heteroatom) provided that a stable compound results.

Unless expressly stated to the contrary, all ranges cited above are inclusive; i.e., the range includes the values for the upper and lower limits of the range as well as all values in between. Thus, for example, a ring described as containing from "1 to 4 heteroatoms" means the ring can contain 1, 2, 3 or 4 heteroatoms. It is also to be understood that the cited range includes within its scope all of the sub-ranges within that range. Thus, for example, a heterocyclic ring described as containing from "1 to 4 heteroatoms" is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, 3 heteroatoms, and 4 heteroatoms. As another example, a ring (e.g., an aryl such as phenyl or naphthyl described as optionally substituted with "from 1 to 4 substituents" is intended to include as aspects thereof, a ring substituted with 1 to 4 substituents, 2 to 4 substituents, 3 to 4 substituents, 4 substituents, 1 to 3 substituents, 2 to 3 substituents, 3 substituents, 1 to 2 substituents, 2 substituents, and 1 substituent.

When any variable occurs more than one time in a compound involved in the process of the invention (e.g., $R^E$ in Compound II), its definition on each occurrence is independent of its definition at every other occurrence. Also, combinations of substituents and/or variables are permissible only if such combinations result in a stable compound.

Unless expressly stated to the contrary, substitution by a named substituent is permitted on any atom in a ring (e.g., cycloalkyl, aryl, or heteroaryl) provided such ring substitution is chemically allowed and results in a stable compound.

In reference to the compounds employed as reactants or reagents in the process of the invention (e.g., Compounds II, III, and IV), a "stable" compound is one whose structure and properties remain or can be caused to remain essentially unchanged for a period of time sufficient to allow its use in the process of the invention so as to achieve the preparation of Compound I. In reference to Compound I, a "stable" compound is a compound which can be prepared in accordance with the process of the present invention and then isolated and whose structure and properties remain or can be caused to remain essentially unchanged for a period of time sufficient to allow use of the compound for its intended purpose; e.g., for the therapeutic administration to a subject who has an HIV infection or AIDS. The process of the present invention is limited to the use and/or preparation of such stable compounds.

Step A of the process of the invention involves the acylation of the free amine in Compound II with acylating agent III to obtain acylated amine IV. Step A is conducted in organic solvent A. Organic solvent A can suitably be an aprotic solvent. The aprotic solvent can be, for example, a haloalkane, a dialkyl ether, a dialkoxyalkane, a bis(alkoxyalkyl)ether, a cyclic ether or diether, an aliphatic nitrile, an aromatic nitrile, or a tertiary carboxylic amide. A class of suitable aprotic solvents consists of $C_1$-$C_4$ haloalkanes, dialkyl ethers wherein each alkyl is independently a $C_1$-$C_4$ alkyl, $C_1$-$C_4$ linear or branched alkanes substituted with two —O—$C_1$-$C_4$ alkyl groups which are the same or different, bis($C_{1-4}$ alkoxy-$C_{1-4}$ alkyl)ethers, $C_4$-$C_8$ cyclic ethers and diethers, $C_2$-$C_4$ aliphatic nitriles, $C_7$-$C_9$ aromatic nitriles, N,N-di-$C_{1-4}$ alkyl $C_{1-4}$ alkylcarboxamides, and tertiary $C_{4-6}$ lactams. In one aspect, the organic solvent employed in Step A is methylene chloride, diethyl ether, MTBE, DME, dimethoxymethane, bis(2-methoxyethyl)ether, THF, dioxolane, dioxane, acetonitrile, propionitrile, benzonitrile, o-tolunitrile, p-tolunitrile, DMF, DMAC, or NMP. In a feature of this aspect, the solvent employed in Step A is acetonitrile, DMF, THF, MTBE or NMP. In another feature of this aspect, the solvent is acetonitrile.

Step A can be conducted at any temperature at which the reaction (acylation) forming Compound IV can detectably proceed. The reaction can suitably be conducted at a temperature in a range of from about −40° C. to about 100° C. and is typically conducted at a temperature in a range of from about −15° C. to about 15° C. In an aspect of the present invention, Step A is conducted at a temperature in a range of from about −5° C. to about 5° C.

The acylation in Step A is conducted in the presence of base. The base employed in Step A can be any base which will neutralize acid by-products of the acylation. The base can be, for example, a metal hydroxide, a metal carbonate, a tertiary amine, or a pyridine. A class of suitable bases consists of alkali metal hydroxides and tertiary amines. A sub-class of suitable bases consists of tri-$C_{1-4}$ alkyl amines and $C_{4-6}$ azacycloalkanes and diazacycloalkanes in which one of the ring carbons is optionally replaced with O or S and wherein each of the ring nitrogens is substituted with $C_{1-4}$ alkyl. In one aspect the base is LiOH, KOH, NaOH, Na carbonate, K carbonate, NMM, NEM, TEA, DIPEA, DABCO, pyridine or collidine. In a feature of this aspect, the base employed in Step A is NMM, NEM, TEA, DIPEA, or DABCO. In another feature of this aspect, the base is NMM.

Compound II, acylation agent III and base can be employed in any amounts which result in the formation of at least some acylated amine IV. Optimal conversion of Compound II and optimal formation of acylated amine IV are normally desired in Step A, and thus the relative proportions of reactants and reagents suitable for this purpose are typically employed. Acylating agent III can suitably be employed in an amount of at least about 0.9 equivalent (e.g., at least about 1 equivalent) per equivalent of the compound of Formula II, is typically employed in an amount in a range of from about 1 to about 5 equivalents per equivalent of Compound II, and is more typically employed in an amount in a range of from about 1 to about 2 equivalents per equivalent of Compound II. In one aspect, acylating agent III is employed in an amount in a range of from about 1 to about 1.5 equivalents per equivalent of Compound II. In another aspect, acylating agent III is employed in an amount in a range of from about 1 to about 1.2 equivalents per equivalent of Compound II.

Although not required, an activating agent (e.g., EDC, DCC or BOP-Cl) can be employed in combination with acylating agent III. When used in Step A, the activating agent is typically employed in an amount of at least one equivalent per equivalent of acylating agent III, and is more typically employed in an amount in a range of from about 1 to 1.5 equivalents per equivalent of acylating agent III.

The base can suitably be employed in an amount of at least about 0.9 equivalent (e.g., at least about 1 equivalent) per equivalent of the compound of Formula II, is typically employed in an amount in a range of from about 1 to about 5 equivalents per equivalent of Compound II, and is more typically employed in an amount in a range of from about 1 to about 2 equivalents per equivalent of Compound II. In one aspect, the base is employed in an amount in a range of from about 1 to about 1.5 equivalents per equivalent of Compound II. In another aspect, the base is employed in an amount in a range of from about 1 to about 1.2 equivalents per equivalent of Compound II.

The reaction time for Step A can vary widely depending upon (i) the choice and relative proportions of Compound II, acylating agent III and base, (ii) the choice of solvent, (iii) the choice of reaction temperature, and (iv) the level of conversion desired. Nonetheless, the reaction can usually be completed (i.e., 100% conversion) in about 24 hours or less (e.g., about 12 hours or less), and is typically complete in about 8 hours or less, and is often complete in about 4 hours or less (e.g., in from about 0.1 to about 2 hours).

The order of addition of the reactants and reagents to the reaction vessel (or reaction "pot") in Step A is not critical. The reactants and reagents can be added concurrently, either together or separately, or they can be added sequentially in any order, or some can be added concurrently and others sequentially prior or subsequent to the concurrent addition. Step A can be conducted, for example, in the following manner: Compound II and aprotic solvent are charged to a flask and brought (e.g., cooled) to reaction temperature, after which the base is added. This admixture is then added to the reaction vessel containing a separately prepared mixture of acylating agent III in aprotic solvent, also at reaction temperature. The reaction mixture is then be aged at the reaction temperature until the desired degree of conversion is achieved. Complete conversion of Compound II is typically desired. The Step A reaction mixture is optionally agitated (e.g., stirred) during addition of the reactants and reagents to the reaction vessel and optionally also during any subsequent ageing. The acylated amine IV formed in Step A can be recovered by conventional means (e.g., precipitating amine IV by addition of water to the reaction mixture and then separating the precipitate by filtration) for use in Step B, or the reaction mixture comprising acylated amine IV can be employed directly in Step B; i.e., Steps A and B can be conducted in the same pot.

Step B of the process of the invention involves the hydrolysis of Compound IV resulting from Step A with aqueous base to obtain Compound I. Step B is conducted in organic solvent B. Organic solvent B can be an aprotic solvent. Organic solvent B can independently be any of the solvents set forth above for use as organic solvent A. Thus, in one aspect, organic solvent B is DCM, diethyl ether, MTBE, DME, dimethoxymethane, bis(2-methoxyethyl)ether, THF, dioxolane, dioxane, acetonitrile, propionitrile, benzonitrile, o-tolunitrile, p-tolunitrile, DMF, DMAC, or NMP. In a feature of this aspect, organic solvent B is acetonitrile, DMF, THF, MTBE, or NMP. In another feature of this aspect, the solvent is acetonitrile.

In another aspect, the solvents employed in Steps A and B are the same; i.e., organic solvent A=organic solvent B. In a feature of the aspect, the solvent employed in Steps A and B is acetonitrile, DMF, THF, MTBE, or NMP. In another feature of this aspect, the solvent employed in Steps A and B is acetonitrile.

Step B can be conducted at any temperature at which the hydrolysis forming Compound I can detectably proceed. The reaction can suitably be conducted at a temperature in a range of from about −30° C. to about 30° C., and is typically conducted at a temperature in a range of from about −5° C. to about 15° C. In an aspect of the present invention, Step B is conducted at a temperature in a range of from about 5° C. to about 10° C.

The aqueous base employed in Step B can be any base which can hydrolyze Compound IV to provide Compound I. The aqueous base can suitably be a metal hydroxide or a quaternary ammonium hydroxide. The term "aqueous" here means that the base is employed as a solution, suspension or dispersion in water. A class of suitable bases consists of alkali metal hydroxides, an alkaline earth metal hydroxides, and ammonium hydroxide. In one aspect, the base employed in Step B is LiOH, NaOH, or KOH. In a feature of this aspect, the base is KOH.

The aqueous base can be employed in any amount which results in the formation of at least some Compound I, but the base is typically employed in an amount that can provide optimal conversion of Compound IV and optimal formation of Compound I. Accordingly, the aqueous base can suitably be employed in an amount of at least about 0.9 equivalent (e.g., at least about 1 equivalent) per equivalent of Compound IV, is typically employed in an amount in a range of from about 1 to about 10 equivalents per equivalent of Compound IV, and is more typically employed in an amount in a range of from about 1 to about 8 equivalents (e.g., from about 2 to about 8 equivalents) per equivalent of Compound IV. In an aspect of the present invention, the base is employed in an amount in a range of from about 2 to about 6 equivalents (e.g., from about 5 to about 6 equivalents) per equivalent of Compound IV. As noted elsewhere, Steps A and B can be conducted in the same reaction vessel without recovery or isolation of the Compound IV formed in Step A; i.e., Process P is conducted as a "one-pot synthesis". In this circumstance, it is convenient to assume that all or substantially all of Compound II was converted into Compound TV in Step A, and then determine the appropriate amount of base to be employed in Step B in terms of a range of equivalents of base per equivalent of Compound II. In this circumstance, the ranges of equivalents of base for use in Step B per equivalent of Compound IV become ranges of equivalents of base per equivalent of Compound II.

The reaction time for Step B can vary widely depending upon (i) the choice of solvent, (ii) the choice and relative proportion of aqueous base, (iii) the choice of reaction temperature, and (iii) the level of conversion desired. The reaction is nonetheless usually complete in about 24 hours or less (e.g., about 12 hours or less), and is typically complete in about 8 hours or less, and is often complete in about 4 hours or less (e.g., in from about 0.1 to about 2 hours).

As indicated above, the reaction parameters (e.g., choice of solvent, amount of solvent, choice of base, amount of base, reaction temperature, and reaction time) typically employed in Step B are those that can result in the substantial conversion of Compound II to Compound I. More particularly, preferred combinations of parameters are those that provide for the hydrolysis of —OC(O)R$^2$ with minimal to no hydrolysis of —N(R$^5$)C(O)R$^6$. Using the information provided herein the person of ordinary skill in the art can identify such combinations of reaction parameters without undue experimentation.

The order of addition of the reactants and reagents to the reaction vessel (or reaction "pot") in Step B is not critical. Step B can be conducted, for example, in the following manner: The aqueous base is added to Compound IV dissolved in organic solvent B (e.g., acetonitrile) at reaction temperature and the mixture is aged at that temperature until the desired degree of conversion (typically 100%) is achieved. The Step B reaction mixture is optionally agitated (e.g., stirred) during addition of the aqueous base and optionally also during the subsequent ageing. Compound I formed in Step B can then be recovered using conventional means. For example, Compound I can be recovered by acidifying the reaction mixture (e.g, with acetic acid), adding water with or without seed to form a crystalline slurry, ageing the slurry, separating the crystalline product by filtration, and washing and then drying the Compound I crystalline product.

Compound IV can be isolated from the product mixture resulting from Step A and then dissolved in organic solvent B for use in Step B. Alternatively and preferably, Compound IV is not isolated from the Step A product mixture but instead the product mixture is used as is with addition of the aqueous base to the product mixture; e.g., the aqueous base can be added directly to the reaction vessel containing the Step A product mixture and Step B conducted therein; i.e., Steps A and B are carried out in a one-pot synthesis. By default, organic solvent A and organic solvent B are the same in the one-pot synthesis.

The present invention also includes a process for preparing a compound of Formula I which comprises Steps A and B as described above, and which further comprises:

(C) contacting a compound of Formula V:

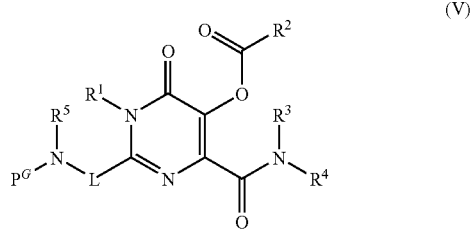

(V)

in organic solvent C with a source of hydrogen in the presence of a hydrogenolysis catalyst to obtain the compound of Formula II; wherein P$^G$ is an amine protective group capable of being cleaved by hydrogenolysis.

Step C is directed to the removal of the amine protective group P$^G$ to provide the free amine N(H)R$^5$ in Compound II.

It is understood that Embodiments E1 to E51 directed to L, R$^1$, R$^2$, R$^3$, R$^4$, R$^5$, R$^6$ and variables incorporated therein (e.g., AryA, AryC, HetQ, R$^E$, etc.) also apply to the process comprising Steps A, B and C. It is also understood that Step C is conducted prior to Step A; i.e., the order of the steps in this process is Step C, followed by Step A, and then Step B.

Amine protective groups capable of being cleaved by hydrognelolysis are well known in the art and include, for example, those described in Greene and Wuts, *Protective Groups in Organic Synthesis,* 3d edition, (Wiley-Interscience, 1999), pp. 494-653 (herein incorporated by reference in its entirety); and in McOmie, *Protective Groups in Organic Synthesis* (Plenum, 1973), pp. 44-74 (herein incorporated by reference in its entirety).

A fifty-second embodiment of the present invention (Embodiment E52) is the process comprising Steps A and B and C, wherein P$^G$ is: (1) C(=O)—O—(CH$_2$)$_{0-1}$—CH=CH$_2$, or (2) C(=O)—O—C$_{1-4}$ alkylene-aryl, where the aryl is optionally substituted with from 1 to 5 substituents each of which is independently halo, —NO$_2$, —C$_{1-4}$ alkyl, or —O—C$_{1-4}$ alkyl; and all other variables are as originally defined or as defined in any of the preceding embodiments.

A fifty-third embodiment of the present invention (Embodiment E53) is the process comprising Steps A and B and C, wherein P$^G$ is: (1) —C(=O)—O—CH$_2$—CH=CH$_2$, or (2) —C(=O)—O—CH$_2$-phenyl, where the phenyl is optionally substituted with from 1 to 3 substituents each of which is independently halo, —NO$_2$, —C$_{1-4}$ alkyl, or —O—C$_{1-4}$ alkyl; and all other variables are as originally defined or as defined in any of the preceding embodiments.

A fifty-fourth embodiment of the present invention (Embodiment E54) is the process comprising Steps A and B and C, wherein P$^G$ is allyloxycarbonyl, benzyloxycarbonyl, p-methoxybenzyloxycarbonyl, p-nitrobenzyloxycarbonyl, p-bromobenzyloxycarbonyl, p-chlorobenzyloxycarbonyl, or 2,4-dichlorobenzyloxycarbonyl; and all other variables are as originally defined or as defined in any of the preceding embodiments.

A fifty-fifth embodiment of the present invention (Embodiment E55) is the process comprising Steps A and B and C, wherein P$^G$ is benzyloxycarbonyl; and all other variables are as originally defined or as defined in any of the preceding embodiments.

Step C is conducted in organic solvent C. Organic solvent C can be, for example, a carboxylic ester, an aliphatic ether or diether, a cyclic ether or diether, an aromatic hydrocarbon, a tertiary carboxylic amide, an alcohol, an alcohol-water mixture, or an alcohol-water-carboxylic ester mixture. A class of suitable solvents consists of C$_{1-4}$ alkyl esters of C$_1$-C$_4$ alkylcarboxylic acids, dialkyl ethers wherein each alkyl is independently a C$_1$-C$_4$ alkyl, C$_1$-C$_4$ linear or branched alkanes substituted with two —O—C$_{1-4}$ alkyl groups which are the same or different, bis(C$_{1-4}$ alkoxy-C$_{1-4}$ alkyl)ethers, C$_4$-C$_8$ cyclic ethers and diethers, toluene, o-xylene, m-xylene, p-xylene, xylene mixtures, N,N-di-C$_{1-4}$ alkyl C$_{1-4}$ alkylcarboxamides, tertiary C$_{4-6}$ lactams, C$_{1-4}$ alkyl alcohols, mixtures of a C$_{1-4}$ alkyl alcohol with water, and mixtures of a C$_{1-4}$ alkyl alcohol and a C$_{1-4}$ alkyl C$_{1-4}$ alkylcarboxylate and water. In one aspect, the solvent employed in Step C is ethyl acetate, isopropyl acetate, diethyl ether, MTBE, DME, dimethoxymethane, bis(2-methoxyethyl)ether, THF, dioxolane, dioxane, toluene, DMF, DMAC, NMP, methanol, ethanol, isopropanol, n-propanol, isobutanol, methanol-water, ethanol-water, or methanol-ethyl acetate-water. In a feature of this aspect, the solvent is a mixture of methanol, ethyl acetate and water.

In another aspect, the solvent employed in Step C is a mixture of water with a $C_{1-3}$ alkyl alcohol and optionally also a $C_{1-3}$ alkyl acetate. In a feature of this aspect the solvent is a water-methanol mixture, a water-ethanol mixture, a water-methanol-ethyl acetate mixture, or a water-methanol-isopropyl acetate mixture. When a mixture of water with an alcohol and optionally with an ester is employed, the water can, for example, comprise from about 5 to about 95 volume percent based on the total volume of solvent.

The hydrogenolysis of Compound V in Step C can be conducted at any temperature at which the reaction (deprotection of the amine) forming Compound II can detectably proceed. The reaction can suitably be conducted at a temperature in a range of from about −50° C. to about 200° C. and is typically conducted at a temperature in a range of from about 0° C. to about 40° C.

The hydrogen source is typically hydrogen gas, optionally in admixture with a carrier gas that is chemically inert under the reaction conditions employed in Step C (e.g., nitrogen or a noble gas such as helium or argon). The pressure is not a critical aspect in Step C, although atmospheric and superatmospheric pressures tend to be expedient. The pressure typically is at least about 2 psig (115 kPa). In one aspect of Step C, the pressure is in a range of from about 2 psig to about 20 psig.

The uptake of hydrogen is not a critical process parameter, although at least a stoichiometric amount of hydrogen gas is typically employed.

The hydrogenolysis catalyst comprises a supported or unsupported Group 8 metal or a supported or unsupported salt or complex of a Group 8 metal. A class of suitable catalysts consists of supported and unsupported metal catalysts selected from the group consisting of Pd, Pt, Rh, Ni and salts thereof. Suitable catalyst supports include carbon, silica, alumina, silicon carbide, aluminum fluoride, and calcium fluoride. In an aspect of Step C, the catalyst is a supported or unsupported Pd or a supported or unsupported Pd salt or complex. In a feature of this aspect, the catalyst is Pd black (i.e., fine metallic palladium particles) or Pd/C (i.e., palladium on a carbon support). In another feature of this aspect, the catalyst is Pd/C.

The hydrogenolysis catalyst can be employed in any amount that allows the reaction to proceed under less extreme conditions and/or in a shorter time compared to the reaction conditions and/or reaction time in the absence of the catalyst. The hydrogenolysis catalyst can suitably be employed in Step C in an amount of at least about 0.01 wt. % relative to the weight of Compound V, is typically employed in an amount in a range of from about 0.01 wt. % to about 100 wt. % relative to the weight of Compound V. In one aspect of Step C, the catalyst is employed in an amount in a range of from about 0.2 wt. % to about 5 wt. %. In another aspect of Step C, the catalyst is employed in an amount in a range of from about 1 wt. % to about 3 wt. %.

Step C can optionally be conducted in the presence of an acid such as glycolic acid, methanesulfonic acid, triflic acid, p-toulenesulfonic acid, acetic acid, TFA, sulfuric acid, or hydrochloric acid. In certain embodiments of the process, the presence of the acid has been observed to reduce the formation of by-products. For example, the presence of an acid has been found to reduce or eliminate the formation of des-fluoro by-products in the hydrogenolysis of N-fluorobenzyl hydroxypyrimidinone carboxamides of Formula V. It has also been observed that the presence of the acid tends to maintain free amine II in solution as a salt (e.g., as a glycolate salt) during the hydrogenation which permits the efficient removal of solid catalyst by filtration. When present, the acid is typically employed in an amount of at least about 0.9 equivalent (e.g., from about 1 to about 10 equivalents, or from about 1 to about 5 equivalents) per equivalent of Compound V.

The hydrogenation can be carried out in batches or continuously in various types of reactors such as a fixed bed reactor or an agitated slurry reactor in which the slurry of gas, solvent, Compound V, catalyst, and (optionally) acid is continuously agitated by mechanical or gas means. A suitable reaction vessel for relatively small scale, batch-wise hydrogenations is an autoclave equipped with a stirrer or rocker to agitate the reaction mixture. In a batch process, the order of addition of Compound V, catalyst, solvent, and (optionally) acid to the reaction vessel is not critical. The reactants and reagents can be added concurrently, either together or separately, or they can be added sequentially in any order, or some can be added concurrently and others sequentially prior or subsequent to the concurrent addition. As an example, Compound V pre-mixed with solvent can be charged to the reaction vessel followed by the addition of catalyst. The hydrogenolysis can then be conducted by charging hydrogen gas, optionally in admixture with one or more inert gases, to the vessel and then agitating the mixture under reaction conditions until the desired degree of conversion is achieved.

Compound V can be prepared from a compound of Formula VI as described in Step D immediately below. As noted below, an organic layer containing Compound V can be extracted from the Step D product mixture and that layer employed directly in Step C; i.e., Compound V is not isolated prior to use in Step C. In this circumstance, it is convenient to assume that all or substantially all of Compound VI is converted into Compound V in Step D, and then determine the appropriate amounts of hydrogen, catalyst, and (optionally) acid to be employed in Step C with respect to Compound VI. In this circumstance, the ranges of weight percent of catalyst, the amounts of hydrogen, and the ranges of equivalents of acid for use in Step C based on Compound V become ranges and amounts based on Compound VI.

The present invention also includes a process for preparing a compound of Formula I which comprises Steps A, B and C as described above, and which further comprises:

(D) contacting a compound of Formula VI:

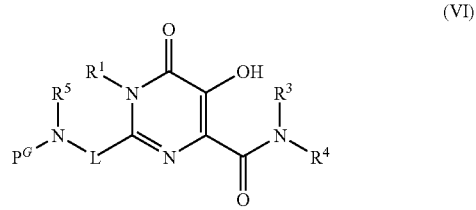

with an esterification agent of Formula VII:

in organic solvent D in the presence of base and optionally in the presence of an esterification catalyst to obtain the compound of Formula V; wherein Y is halogen or $OC(O)R^2$.

Step D is directed to the esterification of the 5-hydroxy group on the pyrimidinone ring of Compound VI. It is understood that Embodiments E1 to E55 set forth above also apply to the process comprising Steps A, B, C and D. It is also understood that Step D is conducted prior to Step C; i.e., the order of the steps in this process is Step D, followed by Step C, followed by Step A, and then Step B.

A fifty-sixth embodiment of the present invention (Embodiment E56) is the process comprising Steps A, B, C and D, wherein Y is halogen; and all other variables are as originally defined or as defined in any one of the preceding embodiments.

A fifty-seventh embodiment of the present invention (Embodiment E57) is the process comprising Steps A, B, C and D, wherein Y is Cl or Br; and all other variables are as originally defined or as defined in any one of the preceding embodiments.

A fifty-eighth embodiment of the present invention (Embodiment E58) is the process comprising Steps A, B, C and D, wherein Y is Cl; and all other variables are as originally defined or as defined in any one of the preceding embodiments.

Step D is conducted in organic solvent D. Organic solvent D can be, for example, a carboxylic ester, an aliphatic ether or diether, a cyclic ether or diether, an aromatic hydrocarbon, a tertiary carboxylic amide, an alcohol, an alcohol-water mixture, or an alcohol-water-carboxylic ester mixture. A class of suitable solvents consists of $C_{1-4}$ alkyl esters of $C_1$-$C_4$ alkylcarboxylic acids, dialkyl ethers wherein each alkyl is independently a $C_1$-$C_4$ alkyl, $C_1$-$C_4$ linear or branched alkanes substituted with two —O—$C_{1-4}$ alkyl groups which are the same or different, bis($C_{1-4}$ alkoxy-$C_{1-4}$ alkyl)ethers, $C_4$-$C_8$ cyclic ethers and diethers, toluene, o-xylene, m-xylene, p-xylene, xylene mixtures, N,N-di-$C_{1-4}$ alkyl $C_{1-4}$ alkylcarboxamides, tertiary $C_{4-6}$ lactams, $C_{1-4}$ alkyl alcohols, mixtures of a $C_{1-4}$ alkyl alcohol with water, and mixtures of a $C_{1-4}$ alkyl alcohol and a $C_{1-4}$ alkyl $C_{1-4}$ alkylcarboxylate and water. In one aspect the solvent employed in Step D is ethyl acetate, isopropyl acetate, diethyl ether, MTBE, DME, dimethoxymethane, bis(2-methoxyethyl)ether, THF, dioxolane, dioxane, toluene, DMF, DMAC, NMP, methanol, ethanol, isopropanol, n-propanol, isobutanol, methanol-water, ethanol-water, and methanol-water-ethyl acetate. In a feature of this aspect, the solvent employed in Step D is EtOAc or IPAc.

In another aspect, the solvent employed in Step D is a mixture of water with a $C_{1-3}$ alkyl alcohol and optionally also a $C_{1-3}$ alkyl acetate. In a feature of this aspect the solvent is a water-methanol mixture, a water-ethanol mixture, a water-methanol-ethyl acetate mixture, or a water-methanol-isopropyl acetate mixture. When a mixture of water with an alcohol and optionally with an ester is employed, the water can, for example, comprise from about 5 to about 95 volume percent based on the total volume of solvent.

The base employed in Step D can be, for example, a metal hydroxide or a tertiary amine. A class of bases suitable for use in Step D consists of alkali metal hydroxides, tertiary alkyl amines, and tertiary cyclic amines and diamines. The base can be, for example, LiOH, NaOH, KOH, a tri-$C_{1-4}$ alkyl amine, or a $C_{4-6}$ azacycloalkane or diazacycloalkane in which one of the ring carbons is optionally replaced with O or S and wherein each of the ring nitrogens is substituted with $C_{1-4}$ alkyl. In one aspect, the base employed in Step D is NaOH, KOH, triethylamine, diisopropylethylamine, N-methylpyrrolidine, N-methylpiperidine, N,N'-dimethylpiperazine, or N-methylmorpholine. In another aspect, the base employed in Step D is a tri-$C_{1-4}$ alkyl amine. In a feature of this aspect, the base is TEA.

Compound VI, esterification agent VII and base can be employed in Step D in any amounts which result in the formation of at least some of Compound V. Optimal conversion of Compound VI and optimal formation of Compound V is normally desired in Step D, and thus the relative proportions of reactants and reagents suitable for this purpose are typically employed. Esterification agent VII can suitably be employed in Step D in an amount of at least about 0.9 equivalent (e.g., at least about 1 equivalent) per equivalent of Compound VI, and is typically employed in an amount in a range of from about 1 to about 10 equivalents per equivalent of Compound VI. In one aspect, the esterification agent VII is employed in Step D in an amount in a range of from about 1 to about 1.5 equivalents per equivalent of Compound VI. Similarly, the base can suitably be employed in Step D in an amount of at least about 0.9 equivalent (e.g., at least about 1 equivalent) per equivalent of Compound VI, and is typically employed D in an amount in a range of from about 1 to about 10 equivalents per equivalent of Compound VI. In one aspect, the base is employed in Step D in an amount in a range of from about 1 to about 1.5 equivalents per equivalent of Compound VI.

An esterification catalyst is optionally employed in Step D. The esterification catalyst can be any catalyst which assists in the esterification of Compound VI and results in the formation of Compound V. Suitable esterification catalysts include diazabicycloalkenes and dialkylaminopyridines. In one aspect, the esterification catalyst is DMAP, DBN, or DBU. In a feature of this aspect, the esterification catalyst is DMAP.

The esterification catalyst can be employed in Step D in any amount that allows the reaction to proceed under less extreme conditions and/or in a shorter time compared to the reaction conditions and/or reaction time in the absence of the catalyst. The esterification catalyst is suitably employed in Step D in an amount in a range of from about zero to 1 equivalent per equivalent of Compound VI, and is typically employed in an amount a range of from about 0.000001 to about 0.1 equivalents per equivalent of Compound VI. In one aspect, the catalyst is employed in Step D in an amount in a range of from about 0.000001 to about 0.01 equivalents per equivalent of Compound VI. In a feature of this aspect, the esterification catalyst is employed in Step D in an amount in a range of from about 0.001 to about 0.01 equivalents per equivalent of Compound VI.

Step D can be conducted at any temperature at which the reaction (esterification) forming Compound V can detectably proceed. The reaction can suitably be conducted at a temperature in a range of from about −20° C. to about 100° C. and is typically conducted at a temperature in a range of from about 0° C. to about 30° C.

The order of addition of the reactants and reagents to the reaction vessel in Step D is not critical. The reactants and reagents can be added concurrently, either together or separately, or they can be added sequentially in any order, or some can be added concurrently and others sequentially prior or subsequent to the concurrent addition. Step D can be conducted, for example, in the following manner: Compound VI and solvent are charged to the reaction vessel, followed by addition of base and then by addition (optional) of esterification catalyst, and the resulting mixture brought to a suitable reaction temperature. The esterification agent is then added to the reaction vessel while maintaining the mixture at reaction temperature. The resulting slurry is then aged at reaction temperature until the desired degree of conversion (typically 100%) is achieved. The Step D reaction mixture is optionally agitated (e.g., stirred) during addition of the reactants and reagents to the reaction vessel and optionally also during the subsequent ageing. Compound V formed in Step D can then be recovered for use in Step C; e.g., the product mixture can be subjected to solvent extraction by adding water, and the resulting organic layer containing Compound V can be employed directly in Step C.

The present invention also includes a process for preparing a compound of Formula I which comprises Steps A, B, C and D as described above, and which further comprises:

(E) contacting a compound of Formula VIII:

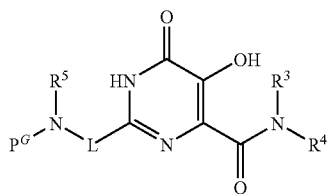

(VIII)

with an alkylating agent in solvent E in the presence of a magnesium base and optionally in the presence of water to obtain the compound of Formula VI; wherein the alkylating agent is:

(1) provided that $R^1$ is methyl, a compound of formula $(CH_3)_3S(O)I$,
(2) provided that $R^1$ is methyl, a compound of formula $(CH_3)_3S(O)Z$, wherein Z is Cl or Br,
(3) a compound of formula $R^1$—I,
(4) a compound of formula $(R^1)_2SO_4$, or
(5) a compound of formula $R^1$-Q, wherein Q is an alkyl sulfonate or an aryl sulfonate;
and provided that when the alkylating agent is $(CH_3)_3S(O)Z$, $(R^1)_2SO_4$, or $R^1$-Q, the agent is employed in combination with an iodide source.

Step E is directed to the alkylation of the nitrogen in position 1 of the pyrimidinone ring of Compound VIII. It is understood that Embodiments E1 to E58 set forth above also apply to the process comprising Steps A, B, C, D and E. It is also understood that Step E is conducted prior to Step D; i.e., the order of the steps in this process is Step E, followed by Step D, then Step C, then Step A and then Step B.

A fifty-ninth embodiment of the present invention (Embodiment E59) is the process comprising Steps A, B, C, D and E, wherein the alkylating agent employed in Step E is $(CH_3)_3S(O)I$ provided that $R^1$ is methyl, $(CH_3)_3S(O)Z$ provided that $R^1$ is methyl, $(C_{1-4}$ alkyl)-I, (AryA-CH$_2$)—I, $(C_{1-4}$ alkyl)$_2$ $SO_4$, AryA-CH$_2SO_4$, $C_{1-4}$ alkyl triflate, $C_{1-4}$ alkyl mesylate, or $C_{1-4}$ alkyl tosylate; provided that when the alkylating agent is $(CH_3)_3S(O)Z$, $(C_{1-4}$ alkyl)$_2SO_4$, AryA-CH$_2SO_4$, $C_{1-4}$ alkyl triflate, $C_{1-4}$ alkyl mesylate, or $C_{1-4}$ alkyl tosylate, the agent is employed in combination with an iodide source; and all other variables are as originally defined or as defined in any one of the preceding embodiments.

A sixtieth embodiment of the present invention (Embodiment E60) is the process comprising Steps A, B, C, D and E, wherein $R^1$ is methyl or benzyl; the alkylating agent employed in Step E is $(CH_3)_3S(O)I$, $(CH_3)_3S(O)Z$, $(CH_3)$—I, (Ph-CH$_2$)—I, $(CH_3)_2SO_4$, Ph-CH$_2SO_4$, methyl triflate, methyl mesylate, or methyl tosylate; provided that when the alkylating agent is $(CH_3)_3S(O)Z$, $(CH_3)_2SO_4$, Ph-CH$_2SO_4$, methyl triflate, methyl mesylate, or methyl tosylate, the agent is employed in combination with an iodide source; and all other variables are as originally defined or as defined in any one of the preceding embodiments.

A sixty-first embodiment of the present invention (Embodiment E61) is the process comprising Steps A, B, C, D and E, wherein $R^1$ is methyl; the alkylating agent employed in Step E is $(CH_3)_3S(O)I$; and all other variables are as originally defined or as defined in any one of the preceding embodiments.

Step E is conducted in organic solvent E. Organic solvent E can suitably be a polar aprotic solvent. The polar aprotic solvent can be, for example, a dialkyl ether, a dialkoxyalkane, a bis(alkoxyalkyl)ether, a cyclic ether or diether, a tertiary alkyl amine, a tertiary cyclic amine or diamine, an aliphatic nitrile, an aromatic nitrile, a tertiary carboxylic amide, a dialkyl sulfoxide, a cyclic sulfone, a N,N-dialkyl cyclic urea, or a hexaalkylphosphoramide. A class of suitable solvents consists of dialkyl ethers wherein each alkyl is independently a $C_1$-$C_4$ alkyl, $C_1$-$C_4$ linear and branched alkanes substituted with two —O—$C_1$-$C_4$ alkyl groups which are the same or different, bis($C_{1-4}$ alkoxy-$C_{1-4}$ alkyl)ethers, $C_4$-$C_8$ cyclic ethers and diethers, $C_2$-$C_4$ aliphatic nitriles, $C_7$-$C_9$ aromatic nitriles, tri-$C_{1-4}$ alkyl amines in which the alkyl groups are the same or different, $C_{4-6}$ azacycloalkanes and diazacycloalkanes in which one of the ring carbons is optionally replaced with O or S and wherein each of the ring nitrogens is substituted with $C_{1-4}$ alkyl, N,N-di-$C_{1-4}$ alkyl $C_{1-4}$ alkylcarboxamides, tertiary $C_{4-6}$ lactams, $C_{4-6}$ cyclic sulfones, N,N'-di-$C_{1-4}$ alkyl-N,N'-(di- or tri- or tetra-methylene)ureas, and hexa($C_{1-4}$ alkyl)phosphoramides.

In one aspect, the solvent employed in Step E is diethyl ether, MTBE, DME, DMM, bis(2-methoxyethyl)ether, THF, dioxolane, dioxane, acetonitrile, propionitrile, benzonitrile, o-tolunitrile, p-tolunitrile, triethylamine, diisopropylethylamine, N methylpyrrolidine, N-methylpiperidine, N-methylmorpholine, DMF, DMAC, NMP, sulfolane, DMPU, or HMPA. In a feature of this aspect, the solvent employed in Step E is NMP or DMAC. In another feature of this aspect, the solvent employed in Step E is NMP.

The base employed in Step E can be a hydroxide, hydride, carbonate, oxide, alkoxide, phosphate, or silicide of magnesium. Grignard reagents (e.g., $C_{1-4}$ alkylmagnesium halides and phenylmagnesium halides) are also suitable. Suitable bases include, for example, Mg(OH)$_2$, MgH$_2$, MgCO$_3$, MgO, Mg(—O—$C_{1-4}$ alkyl)$_2$, mono- or di- or tri-basic (Mg)$_3$(PO$_4$)$_2$, (Mg)$_2$Si, $C_{1-4}$ alkylmagnesium chloride (e.g., MeMgCl) and $C_{1-4}$ alkylmagnesium bromide (e.g., MeMgBr). In one aspect the base employed in Step E is Mg(OH)$_2$, MgO, or Mg(O-t-Bu)$_2$. In a feature of this aspect, the base employed in Step E is Mg(OH)$_2$.

The iodide source employed in Step E in combination with an alkylating agent of formula $(CH_3)_3S(O)Z$, $(R^1)_2SO_4$, or $R^1$-Q can suitably be a metal iodide or a quaternary ammonium iodide. The iodide source can, for example, be selected from the group consisting of alkali metal iodides and tetraalkylammonium iodides. In one aspect, the iodide source is LiI, NaI, KI, or tetra-n-butylammonium iodide. In a feature of this aspect, the iodide source is NaI or KI.

Compound VIII, the alkylating agent and base can be employed in any amounts which result in the formation of at least some of Compound VI. Optimal conversion of Compound VIII and optimal formation of Compound VI is normally desired in Step E, and thus the relative proportions of reactants and reagents suitable for this purpose are typically employed. The alkylating agent can suitably be employed in Step E in an amount of at least about 0.9 equivalent (e.g., at least about 1 equivalent per equivalent of Compound VIII, and is typically employed in an amount in a range of from about 1 to about 10 equivalents per equivalent of Compound VIII. In one aspect, the alkylating agent is employed in Step E in an amount in a range of from about 1.1 to about 5 equivalents per equivalent of Compound VIII. In another aspect, the alkylating agent is employed in Step E in an amount in a range of from about 1.5 to about 3 equivalents per equivalent of Compound VIII.

Similarly, the base can suitably be employed in Step E in an amount of at least about 0.9 equivalent (e.g., at least about 1 equivalent) per equivalent of Compound VIII, and is typically employed in an amount in a range of from about 1 to about 10 equivalents per equivalent of Compound VIII. In one aspect, the base is employed in Step E in an amount in a range of from about 1.1 to about 5 equivalents per equivalent of Compound VIII. In one aspect, the base is employed in Step E in an amount in a range of from about 1.5 to about 3 equivalents per equivalent of Compound VIII.

When an iodine source is required it can suitably be employed in an amount in a range of from about 0.1 to 5 equivalents per equivalent of Compound VIII, and is typically employed in an amount of from about 1 to about 3 equivalents per equivalent of Compound VIII.

Water is optionally employed in Step E. The presence of water can improve reproducibility; e.g., the presence of water has been observed to improve reproducibility of the alkylation step in the preparation of Compound A. Water can suitably be employed in an amount of from about zero to about 2 equivalents per equivalent of Compound VIII. In one aspect, water is employed in Step E in an amount in a range of from about 0.2 to about 1.5 equivalents per equivalent of Compound VIII.

Step E can be conducted at any temperature at which the reaction (alkylation) forming Compound VI can detectably proceed. The reaction can suitably be conducted at a temperature in a range of from about 50° C. to about 130° C. and is typically conducted at a temperature in a range of from about 60° C. to about 120° C. In one aspect, the reaction of Step E is conducted at a temperature in a range of from about 95° C. to about 110° C.

The order of addition of the reactants and reagents to the reaction vessel in Step E is not critical. The reactants and reagents can be added concurrently, either together or separately, or they can be added sequentially in any order, or some can be added concurrently and others sequentially prior or subsequent to the concurrent addition. Step E can be conducted, for example, in the following manner: Solvent is charged to the reaction vessel at a temperature below reaction temperature, followed by the sequential addition of Compound VIII, base, alkylation catalyst, and (optionally) water while maintaining the temperature below reaction temperature. The resulting mixture can then optionally be degassed and then warmed to a suitable reaction temperature and aged at that temperature until the desired degree of conversion (typically 100%) is achieved, after which it is allowed to cool to room temperature. The Step E reaction mixture is optionally agitated (e.g., stirred) during addition of the reactants and reagents to the reaction vessel and optionally also during the subsequent ageing. Compound VI formed in Step E can then be recovered for use in Step D; e.g., the cooled reaction mixture can be quenched with acid, neutralized with an aqueous buffer, and aged to provide a slurry, after which desired solid product is obtained by filtration and then washed and dried.

Compounds of Formula VIII can be prepared by coupling amines of formula $HN(R^3)R^4$ with carboxylates of Formula IX:

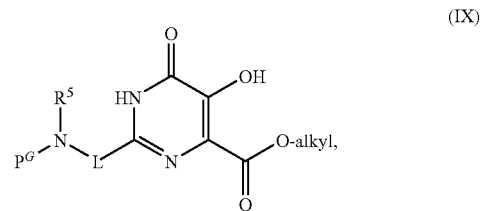

(IX)

which in turn can be prepared in accordance with methods disclosed US 2006/0122205 and WO 03/035077, the disclosures of which are herein incorporated in their entireties.

The present invention also includes a process for preparing Compound A (hereinafter alternatively referred to as Process P'):

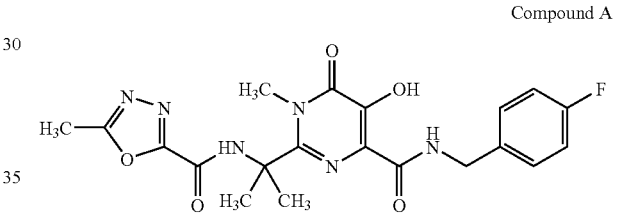

Compound A which comprises:

(A') contacting a compound of Formula II-A:

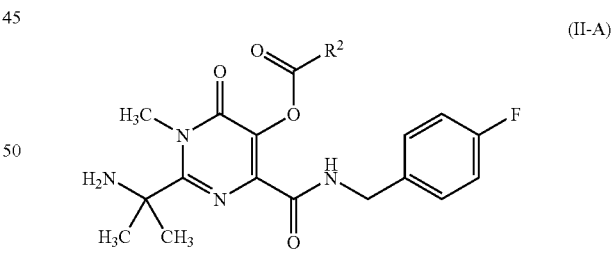

(II-A)

with an acylating agent of Formula III-A:

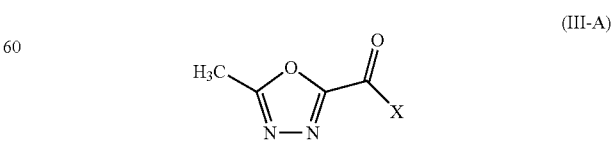

(III-A)

in organic solvent A' in the presence of base to obtain an acylated amine compound of Formula IV-A:

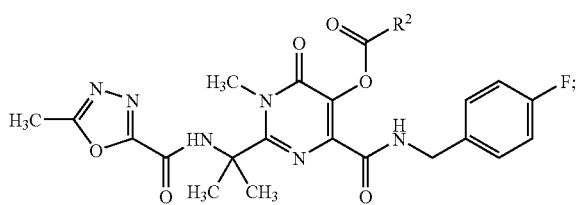

(IV-A)

and (B') contacting the compound of Formula IV-A with an aqueous base in organic solvent B' to obtain Compound A; wherein X is halogen; and $R^2$ is $C_{1-8}$ alkyl or phenyl.

Aspects of Process P' include the process as originally described incorporating one or more of features (a1) to (a9) and (b1) to (b5) as follows:
(a1-a) X is Cl or Br;
(a1-b) X is Cl;
(a2-a) $R^2$ is branched $C_{3-6}$ alkyl or phenyl;
(a2-b) $R^2$ is t-butyl;
(a3-a) Step A' and Step B' are conducted in the same pot wherein organic solvent A' and organic solvent B' are the same solvent;
(a3-b) Step A' and Step B' are conducted in the same pot wherein Step B'comprises adding the aqueous base (e.g., aqueous KOH) to the reaction mixture resulting from Step A' and adjusting as necessary the temperature of the admixture to carry out Step B';
(a4) Step A' is conducted at a temperature in a range of from about −15° C. to about 15° C.;
(a5-a) organic solvent A' is an aprotic solvent which is acetonitrile, THF, DMF, DMAC, MTBE, or NMP;
(a5-b) Step A' is conducted in acetonitrile as solvent;
(a6-a) the base employed in Step A' is NMM, NEM, TEA, DIPEA, or DABCO;
(a6-b) the base employed in Step A' is NMM;
(a7-a) the acylating agent of Formula III-A in Step A' is employed in an amount in a range of from about 1 to about 5 equivalents per equivalent Compound II-A;
(a7-b) the acylating agent of Formula III-A in Step A' is employed in an amount in a range of from about 1 to about 2 equivalents per equivalent Compound II-A;
(a7-c) the acylating agent of Formula III-A in Step A' is employed in an amount in a range of from about 1 to about 1.2 equivalents per equivalent Compound II-A;
(a8-a) the base in Step A' is employed in an amount in a range of from about 1 to about 5 equivalents per equivalent of Compound II-A;
(a8-b) the base in Step A' is employed in an amount in a range of from about 1 to about 2 equivalents per equivalent of Compound II-A;
(a8-c) the base in Step A' is employed in an amount in a range of from about 1 to about 1.2 equivalents per equivalent of Compound II-A;
(a9-a) Step A' is optionally conducted in the presence of an activating agent;
(a9-b) Step A' is optionally conducted in the presence of an activating agent selected from EDC, DCC and BOP-Cl;
(b1-a) the aqueous base employed in Step B' is an alkali metal hydroxide;
(b1-b) the aqueous base employed in Step B' is KOH;
(b2-a) the aqueous base is employed in Step B' in an amount in a range of from about 1 to about 8 equivalents per equivalent of the compound of Formula IV;
(b2-b) the aqueous base is employed in Step B' in an amount in a range of from about 2 to about 6 equivalents per equivalent of the compound of Formula IV;
(b3-a) organic solvent B' is acetonitrile, DMF, THF, MTBE, or NMP;
(b3-b) Step B' is conducted in acetonitrile as solvent;
(b4) the same solvent is employed in Steps A' and B';
(b5) Step B' is conducted at a temperature in a range of from about −5° C. to about 15° C.

It is understood that each of the features (a1) to (a9) and (b1) to (b5) can be incorporated singly or multiply in any combination into Process P' as originally described and that the process resulting from each such incorporation is an aspect of Process P'.

A first embodiment of Process P' (Embodiment P'-E1) comprises Steps A' and B' as originally described, and further comprises:
(C') contacting a compound of Formula V-A:

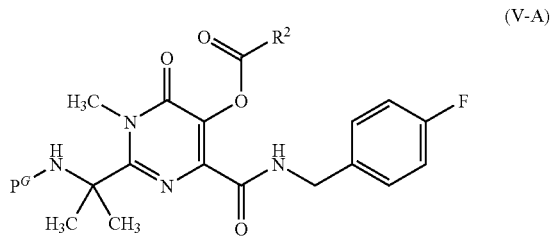

(V-A)

in organic solvent C' with a source of hydrogen in the presence of a hydrogenolysis catalyst to obtain the compound of Formula II-A; wherein $P^G$ is an amine protective group capable of being cleaved by hydrogenolysis. It is understood that Step C' is conducted prior to Step A'; i.e., the order of the steps in this process is Step C', followed by Step A', and then Step B'.

Features of Step C' include the following:
(c1-a) $P^G$ is allyloxycarbonyl, benzyloxycarbonyl, p-methoxybenzyloxycarbonyl, p-nitrobenzyloxycarbonyl, p-bromobenzyloxycarbonyl, p-chlorobenzyloxycarbonyl, or 2,4-dichlorobenzyloxycarbonyl;
(c1-b) $P^G$ is benzyloxycarbonyl;
(c2-a) organic solvent C' is ethyl acetate, isopropyl acetate, diethyl ether, MTBE, DME, dimethoxymethane, bis(2-methoxyethyl)ether, THF, dioxolane, dioxane, toluene, DMF, DMAC, NMP, methanol, ethanol, isopropanol, n-propanol, isobutanol, methanol-water, ethanol-water, or methanol-ethyl acetate-water;
(c2-b) organic solvent C' is a mixture of methanol and ethyl acetate and water;
(c3) the hydrogen source in Step C' is hydrogen gas optionally in admixture with an inert carrier gas;
(c4-a) the hydrogenolysis catalyst in Step C' is supported or unsupported Pd or Pd salt;
(c4-b) the hydrogenolysis catalyst in Step C' is Pd/C;
(c5) the hydrogenolysis catalyst is employed in Step C' in an amount in a range of from about 0.2 wt. % to about 5 wt. %;
(c6-a) Step C' is conducted in the presence of an acid which is glycolic acid, methanesulfonic acid, triflic acid, p-toulenesulfonic acid, acetic acid, TFA, sulfuric acid, or hydrochloric acid;
(c6-b) Step C' is conducted in the presence of glycolic acid;
(c7-a) the acid set forth in (c6-a) or (c6-b) is employed in an amount of from about 1 to about 10 equivalents per equivalent of Compound V-A; and (c7-b) the acid set forth in (c6-a) or (c6-b) is employed in an amount of from about 1 to about 5 equivalents per equivalent of Compound V-A; and (c8) Step C' is conducted at a temperature in a range of from about 0° C. to about 40° C.

Aspects of Embodiment P'-E1 include the process set forth in Embodiment P'-E1 as originally described incorporating one or more of features (a1) to (a9), (b1) to (b5), and (e1) to (c8) as set forth above. It is understood that each of these features can be incorporated singly or multiply in any combination into the process of Embodiment P'-E1 as originally described and that the process resulting from each such incorporation is an aspect of Embodiment P'-E1.

A second embodiment of Process P' (Embodiment P'-E2) comprises Steps A', B' and C' as originally described, and further comprises:

(D') contacting a compound of Formula VI-A:

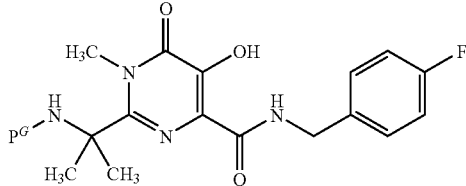

(VI-A)

with an esterification agent of Formula VII:

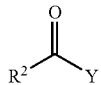

(VII)

in organic solvent D' in the presence of base and optionally in the presence of an esterification catalyst to obtain the compound of Formula V-A; wherein Y is halogen or $OC(O)R^2$. It is understood that Step D' is conducted prior to Step C'; i.e., the order of the steps in this process is Step D', then Step C', followed by Step A', and then Step B'.

Features of Step D' include the following:
(d1-a) Y is Cl or Br;
(d1-b) Y is Cl;
(d2-a) organic solvent D' is ethyl acetate, isopropyl acetate, diethyl ether, MTBE, DME, dimethoxymethane, bis(2-methoxyethyl)ether, THF, dioxolane, dioxane, toluene, DMF, DMAC, NMP, methanol, ethanol, isopropanol, n-propanol, isobutanol, methanol-water, ethanol-water, or methanol-water-ethyl acetate;
(d2-b) organic solvent D' is EtOAc or IPAc;
(d3-a) the base employed in Step D' is tri-$C_{1-4}$ alkylamine;
(d3-b) the base employed in Step D' is TEA;
(d4-a) the optional esterification catalyst employed in Step D' is DMAP, DBN, or DBU;
(d4-b) the optional esterification catalyst employed in Step D' is DMAP;
(d5) the esterification agent VII is employed in Step D' in an amount in a range of from about 1 to about 10 equivalents per equivalent of Compound VI-A;
(d6) the base is employed in Step D' in an amount in a range of from about 1 to about 10 equivalents per equivalent of Compound VI-A;
(d7) when employed, the esterification catalyst is employed in Step D' in an amount in a range of from about 0.000001 to about 0.01 equivalents per equivalent of Compound VI-A;

(d8) Step D' is conducted at a temperature in a range of from about 0° C. to about 30° C.; and (d9) Compound VI-A is recovered from the Step D' reaction mixture as a slurry, suspension or solution in organic solvent D' (e.g., by adding water to the reaction mixture and then cutting the resulting aqueous layer) and used directly in Step C'.

Aspects of Embodiment P'-E2 include the process set forth in Embodiment P'-E2 as originally described incorporating one or more of features (a1) to (a9), (b1) to (b5), (e1) to (c8) and (d1) to (d9) as set forth above. It is understood that each of these features can be incorporated singly or multiply in any combination into the process of Embodiment P'-E2 as originally described and that the process resulting from each such incorporation is an aspect of Embodiment P'-E2.

A third embodiment of Process P' (Embodiment P'-E3) comprises Steps A', B', C' and D' as originally described, and further comprises:

(E') contacting a compound of Formula VIII-A:

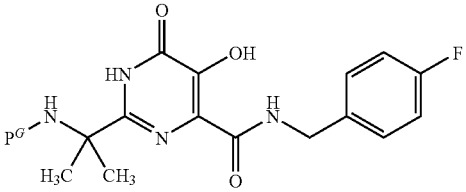

(VIII-A)

with a methylating agent in organic solvent E', in the presence of a magnesium base, and optionally in the presence of water, to obtain the compound of Formula VI-A; wherein the methylating agent is: (1) $(CH_3)_3S(O)I$, (2) $(CH_3)_3S(O)Z$, wherein Z is Cl or Br, (3) $CH_3I$, (4) $(CH_3)_2SO_4$, or (5) a compound of formula $CH_3$-Q, wherein Q is an alkyl sulfonate or an aryl sulfonate; and provided that when the methylating agent is $(CH_3)_3S(O)Z$, $(CH_3)_2SO_4$, or $CH_3$-Q, then the agent is employed in combination with an iodide source. It is understood that Step E' is conducted prior to Step D'; i.e., the order of the steps in this process is Step E', followed by Step D', then Step C', then Step A' and then Step B'.

Features of Step E' include the following:
(e1) the methylating agent employed in Step E is $(CH_3)_3S(O)I$;
(e2-a) the base employed in Step E' is $Mg(OH)_2$, MgO, or $Mg(O-t-Bu)_2$;
(e2-b) the base employed in Step E' is $Mg(OH)_2$;
(e3-a) organic solvent E' is a polar aprotic solvent which is diethyl ether, MTBE, DME, DMM, bis(2-methoxyethyl)ether, THF, dioxolane, dioxane, acetonitrile, propionitrile, benzonitrile, o-tolunitrile, p-toluenitrile, triethylamine, diisopropylethylamine, N methylpyrrolidine, N-methylpiperidine, N-methylmorpholine, DMF, DMAC, NMP, sulfolane, DMPU, or HMPA;
(e3-b) organic solvent E' is NMP or DMAC;
(e3-c) organic solvent E' is NMP;
(e4) the iodide source employed in Step E' is LiI, NaI, KI, or tetra-n-butylammonium iodide;
(e5) the methylating agent and base are each independently employed in Step E' in an amount in a range of from about 1 to about 10 equivalents per equivalent of Compound VIII-A;
(e6) the iodide source is employed in Step E' in an amount in a range of from about 0.1 to 5 equivalents per equivalent of Compound VIII-A;

(e7) when employed, water is employed in Step E' in an amount in a range of from about 0.2 to about 1.5 equivalents per equivalent of Compound VIII-A; and (e8) Step E' is conducted at a temperature in a range of from about 60° C. to about 120° C.

Aspects of Embodiment P'-E3 include the process set forth in Embodiment P'-E3 as originally described incorporating one or more of features (a1) to (a9), (b1) to (b5), (c1) to (c8), (d1) to (d9) and (e1) to (e8) as set forth above. It is understood that each of these features can be incorporated singly or multiply in any combination into the process of Embodiment P'-E3 as originally described and that the process resulting from each such incorporation is an aspect of Embodiment P'-E3.

The advantages of Process P' for making Compound A relative to the processes disclosed in US 2006/0122205 and in WO 03/035077 include the following:

(i) Process P' requires less of the relatively expensive oxadiazolyl coupling agent. More particularly, Process P' requires 1 equivalent of coupling agent per equivalent of amine for 100% conversion, whereas the U.S. '205 process in requires 2 equivalents.

(ii) Substrate II-A containing a free amine and an esterified hydroxy group in Step A' can be crystalline, stable and not hydrated, whereas the corresponding amine-dihydroxy substrates in U.S. '205 and WO '077 can be dihydrates that are difficult to dry.

(iii) Step E' involves methylation of N-4-fluorobenzyl amide VIII-A, whereas the U.S. '205 process involves methylation of the corresponding methyl carboxylate (i.e., compound e in Example 1, Step 5 of U.S. '205). Methylation of amide VIII-A has been found to provide significantly higher yields of N-methylated product (about 99%) than have been achieved using the corresponding carboxylate substrate under analogous reaction conditions (about 80%). While not wishing to be bound by any particular theory, it is believed that methylation of the methyl carboxylate in accordance with U.S. '205 results in the formation of methyl carbamates due to the loss of the CBZ group, the demethylation of the ester, and the formation of O-methylated by-products, all of which reduce the yield of the desired N-methylated product. In contrast, the N-4-fluorobenzyl amide substrate in Step E' is relatively stable under methylation conditions resulting in little or no substrate loss. In addition, to the extent that O-methylation of the N-4-fluorobenzyl amide substrate occurs in Step E' it is believed to be cleaved back to the starting substrate which is then re-methylated to the desired N-methylated product. As a result, Step E' can provide essentially complete conversion to the desired N-methylated product.

The present invention also includes a process for preparing Compound A (hereinafter alternatively referred to as Process P''') which comprises:

(A'') contacting a compound of Formula

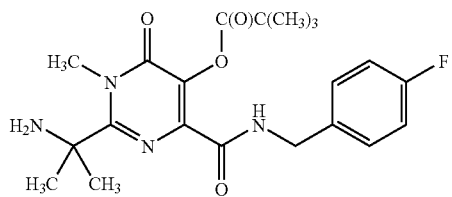

ii-a in acetonitrile with at least about 1 equivalent (e.g., from about 1 to about 5 equivalents, or from about 1 to about 2 equivalents, or from about 1 to about 1.2 equivalents) per equivalent of compound ii-a of an acylating agent of Formula iii-a:

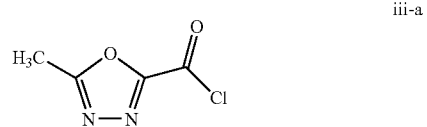

iii-a and in the presence of at least about 1 equivalent (e.g., from about 1 to about 5 equivalents, or from about 1 to about 2 equivalents, or from about 1 to about 1.2 equivalents) of NMM per equivalent of compound ii-a at a temperature in a range of from about −15° C. to about 15° C. to obtain an acylated amine of Formula iv-a:

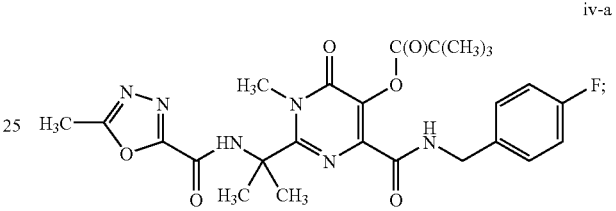

iv-a and (B'') contacting the acylated amine iv-a with at least about 1 equivalent (e.g., from about 1 to about 8 equivalents, or from about 2 to about 6 equivalents) of aqueous KOH per equivalent of compound ii-a in acetonitrile at a temperature in a range of from about −5° C. to about 15° C. to obtain Compound A.

A first embodiment of Process P''' (Embodiment P'''-E1) comprises Steps A'' and B'' as originally described, wherein Steps A'' and B'' are conducted in the same pot. In an aspect of this embodiment, Step B'' comprises adding the aqueous KOH to the reaction mixture resulting from Step A'' and adjusting as necessary the temperature of the admixture to be in the range of from about −5° C. to about 15° C.

A second embodiment of Process P''' (Embodiment P'''-E2) comprises Steps A'' and B'' as originally described or as described in Embodiment P'''-E1, and further comprises:

(C'') contacting a compound of Formula v-a:

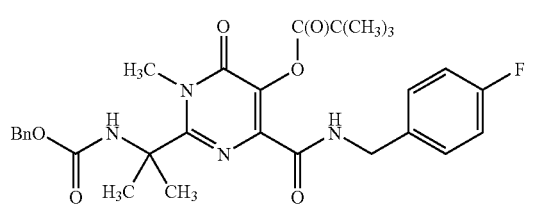

v-a with a source of hydrogen in methanol optionally in admixture with water or with water and ethyl acetate, in the presence of a supported or unsupported Pd or Pd salt as catalyst (e.g., Pd/C), and in the presence of at least about 1 equivalent (e.g., from about 1 to about 10 equivalents, or from about 1 to about 5 equivalents) of glycolic acid per equivalent of compound v-a to obtain the compound of Formula ii-a. It is understood that Step C" is conducted prior to Step A"; i.e., the order of the steps in this process is Step C", followed by Step A", and then Step B".

A third embodiment of Process P" (Embodiment P"-E3) comprises Steps A", B" and C" as originally described in Embodiment P"-E2, and further comprises:

(D") contacting a compound of Formula vi-a:

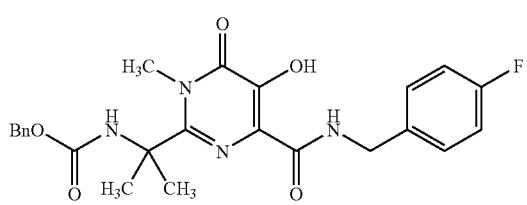

vi-a with at least about 1 equivalent (e.g., from about 1 to about 10 equivalents, or from about 1 to about 1.5 equivalents) of pivaloyl chloride per equivalent of compound vi-a in ethyl acetate at a temperature in a range of from about 0° C. to about 30° C., in the presence of at least about 1 equivalent of triethylamine (e.g., from about 1 to about 10 equivalents, or from about 1 to about 1.5 equivalents) per equivalent of compound vi-a and in the presence of an esterification catalyst selected from DMAP, DBN and DBU (e.g., DMAP), to obtain the compound of Formula v-a. It is understood that Step D" is conducted prior to Step C"; i.e., the order of the steps in this process is Step D", followed by Step C", then Step A", and then Step B".

In an aspect of this embodiment, compound v-a is recovered from the Step D" reaction mixture as a slurry, suspension or solution in ethyl acetate which is used directly in Step C".

A fourth embodiment of Process P" (Embodiment P"-E4) comprises Steps A", B", C" and D" as originally described in Embodiment P"-E3, and further comprises:

(E") contacting a compound of Formula viii-a:

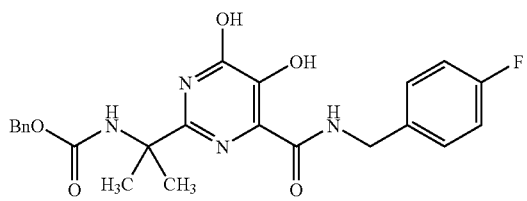

viii-a with at least about 1 equivalent (e.g., from about 1 to about 10 equivalents, or from about 1.1 to about 5 equivalents) of $(CH_3)_3S(O)I$ per equivalent of compound viii-a in NMP at a temperature in a range of from about 95° C. to about 110° C., in the presence of at least about 1 equivalent (e.g., from about 1 to about 10 equivalents, or from about 1.1 to about 5 equivalents) of $Mg(OH)_2$ per equivalent of compound viii-a and in the presence of at least about 0.1 equivalent (e.g., from about 0.2 to about 1.5 equivalents) of water per equivalent of compound viii-a, to obtain a compound of Formula vi-a. It is understood that Step E" is conducted prior to Step D"; i.e., the order of the steps in this process is Step E", followed by Step D", then Step C", then Step A", and then Step B".

The advantages of Process P" for making Compound A relative to the process disclosed in US 2006/0122205 include the following:

(i) Process P" requires less of the relatively expensive oxadiazolyl coupling agent. More particularly, Process P" requires 1 equivalent of coupling agent per equivalent of amine for 100% conversion, whereas the U.S. '205 process in requires 2 equivalents (e.g., compare the use of 1.15 equivalents of coupling agent in Step 5 of Example 1 herein to the use of 2.2 equivalents in Example 1, Step 8, paragraph [0309] of U.S. '205).

(ii) The amine pivalate ii-a employed in Step A" is crystalline, stable and not hydrated, whereas the corresponding amine dihydroxy substrate (compound h in Step 7 of Example 1 in U.S. '205) is a dihydrate that is difficult to dry.

(iii) Steps A" and B" are simpler and provide a higher yield than the corresponding step in U.S. '205. For example, the overall yield of Step 5 (=Steps A" and B") in Example 1 herein is 97% compared to 91% for the corresponding coupling step in Example 1, Step 8, paragraph [0311] of U.S. '205. Further, the U.S. '205 process employs THF which must be removed (e.g., by distillation) in order to isolate Compound A, whereas Step A" employs acetonitrile which does not require removal.

(iv) The protected amine pivalate v-a requires less Pd catalyst in Step C" to remove the Cbz group than the corresponding protected amine dihydroxy substrate (compound g in Step 7 of Example 1 in U.S. '205).

(v) The use of glycolic acid in Step C" has been found to be more effective in reducing the formation of des-fluoro by-product in comparison to the methanesulfonic acid employed in Example 1, Step 7, paragraph [0303] of U.S. '205 and to facilitate the removal by filtration of the Pd catalyst by maintaining amine pivalate ii-a in solution.

(vi) Step E" involves methylation of N-4-fluorobenzyl amide viii-a, whereas the U.S. '205 process involves methylation of the corresponding methyl carboxylate. Step E" provides an improved yield (e.g., 89% yield in Step 2 of Example 1 herein) compared to corresponding step 5 in Example 1 in U.S. '205 (70% yield). Without wishing to be bound by any particular theory, the significant improvement in yield in Step E" is believed to be due to the reasons set forth above in item iii of the paragraph describing advantages of Process P'.

(vii) The methylation in Step E" employing $(CH_3)_3S(O)I$ and $Mg(OH)_2$ in NMP solvent is an improvement over the corresponding step in U.S. '205 using MeI and $Mg(OCH_3)_2$ in DMSO. $(CH_3)_3S(O)I$ is safer to use than the highly toxic and relatively volatile MeI. $Mg(OH)_2$ is less costly and easier to handle than the more reactive $Mg(OCH_3)_2$. The use of NMP as solvent has been found to provide a more reproducible and complete reaction.

The present invention also includes a compound selected from the group consisting of:

(i) a compound of Formula II:

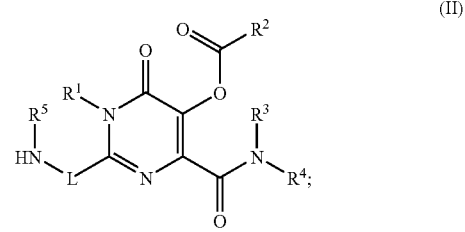

(II)

(ii) a compound of Formula IV:

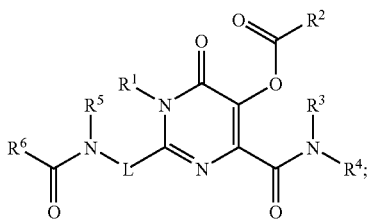

(IV)

(iii) a compound of Formula V:

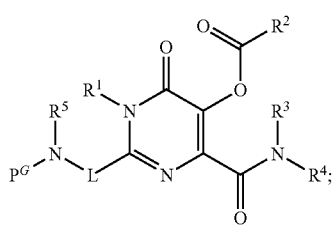

(V)

and pharmaceutically acceptable salts thereof;

wherein L, $R^1$, $R^2$, $R^3$, $R^4$, $R^5$ and $R^6$, are as originally defined in the Summary of the Invention and $P^G$ is an amine protective group capable of being cleaved by hydrogenolysis. Aspects of the invention include Compound II incorporating any one or more of the preceding embodiments of L, $R^1$, $R^2$, $R^3$, $R^4$ and $R^5$ and embodiments defining variables incorporated therein. Other aspects of the invention include Compound IV incorporating any one or more of the preceding embodiments of L, $R^1$, $R^2$, $R^3$, $R^4$, $R^5$ and $R^6$ and embodiments defining variables incorporated therein. Still other aspects of the invention include Compound V incorporating any one or more of the preceding embodiments of L, $R^1$, $R^2$, $R^3$, $R^4$, $R^5$ and $P^G$. It is understood that the incorporation of any of the preceding embodiments individually or in combination in any one of Compounds II, IV and V is an aspect of the invention. Aspects in which $R^2$ is a branched $C_{3-6}$ alkyl are of particular interest.

The present invention also includes a compound selected from the group consisting of:

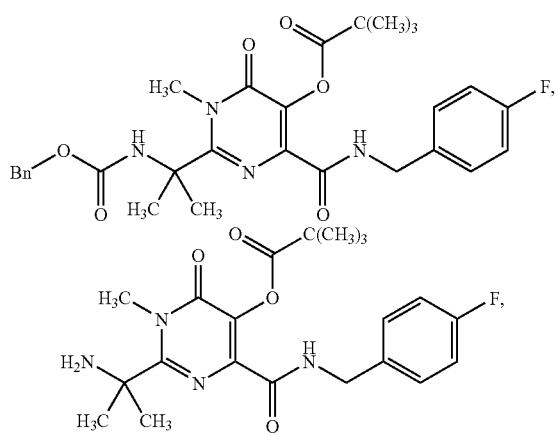

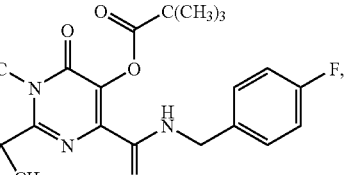

and pharmaceutically acceptable salts thereof.

The progress of any reaction step set forth herein can be followed by monitoring the disappearance of a reactant (e.g., Compound II in Step A) and/or the appearance of the desired product (e.g., Compound I in Step A) using such analytical techniques as TLC, HPLC, IR, NMR or GC.

The term "organic solvent" in reference to any of the organic solvents employed in a reaction or treatment step set forth herein refers to any organic substance, optionally employed with water as a co-solvent, which under the reaction conditions employed in the step of interest is in the liquid phase, is chemically inert, and will dissolve, suspend, and/or disperse the reactants and any reagents so as to bring the reactants and reagents into contact and to permit the reaction to proceed.

The term "ageing" and variants thereof (e.g., "aged") mean allowing the reactants in a given reaction or treatment step to stay in contact for a time and under conditions effective for achieving the desired degree of conversion. The terms "ageing" and variants thereof (e.g., "aged" are used herein interchangeably with the expression "maintaining at reaction temperature until the desired degree of conversion is achieved" and variants thereof (e.g., "maintained ...")

Abbreviations employed herein include the following: Alloc=allyloxycarbonyl; Bn=benzyl; BOP-Cl=benzotriazol-1-yloxytris-(dimethylamino)phosphonium chloride; CBZ or CBz or Cbz=carbobenzoxy (alternatively, benzyloxycarbonyl); DABCO=1,4-diazabicyclo[2.2.2]octane; DBN=1,5-diazabicyclo[4.3.0]non-5-ene; DBU=1,8-diazabicyclo[5.4.0]undec-7-ene; DCC=dicyclohexyl carbodiimide; DIPEA=diisopropylethylamine; DMAC=N,N-dimethylacetamide; DMAP=4-dimethylaminopyridine; DME=1,2-dimethoxyethane; DMF=dimethylformamide; DMM=dimethoxymethane; DMPU=N,N'-dimethylpropyleneurea; DMSO=dimethyl sulfoxide; eq(s).=molar equivalent(s); EDC=1-ethyl-3-(3-dimethylaminopropyl) carbodiimide; EtOAc=ethyl acetate; EtOH=ethanol; HIV=human immunodeficiency virus; HMPA=hexamethylphosphoramide; HPLC=high performance liquid chromatography; IPAc=isopropyl acetate; Me=methyl; MTBE=methyl tert-butyl ether; MeCN=acetonitrile; MeOH=methanol; MSA=methanesulfonic acid; NEM=N-ethylmorpholine; NMM=N-methylmorpholine; NMP=N-methylpyrrolidinone; NMR=nuclear magnetic resonance; Ph=phenyl; TEA=triethylamine; TFA=trifluoroacetic acid; THF=tetrahydrofuran.

The following example serves only to illustrate the invention and its practice. The example is not to be construed as a limitation on the scope or spirit of the invention.

The HPLC method used to assay Compounds 1 to 5 in the example is as follows: Column=Zorbax SB C-18 (25 cm×4.6 mm); flow rate=1.0 mL/minute; detection=210 nm; temperature=30° C.; Solvent A=acetonitrile, B=0.1M aqueous H₃PO₄; gradient elution=20% A: 80% B for 5 minutes, then to 80% A: 20% B at 10 minutes hold 10 minutes.

EXAMPLE 1

Preparation of Compound A

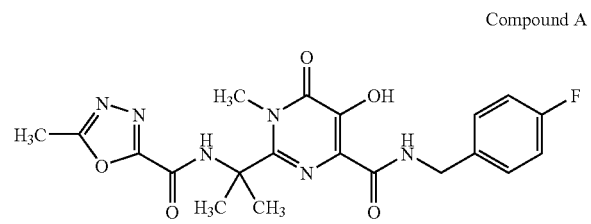 [SMILES: Cc1nnc(C(=O)NC(C)(C)c2nc(C(=O)NCc3ccc(F)cc3)c(O)c(=O)n2C)o1]

Compound A

Step 1: Preparation of benzyl 1-(4-{[(4-fluorobenzyl)amino]carbonyl}-5,6-dihydroxy-1,6-dihydropyrimidin-2-yl)-1-methylethylcarbamate (Compound 2)

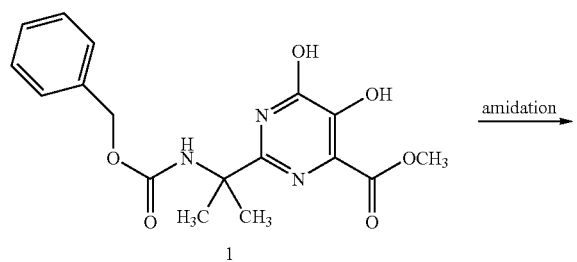

A round bottom flask was charged with methyl 2-(1-{[(benzyloxy)carbonyl]amino}-1-methylethyl)-5,6-dihydroxypyrimidine-4-carboxylate (Compound 1; 1 eq.) and methanol (~1.6 mL per gram of Compound 1). The slurry was warmed to 55° C., after which triethylamine (1.2 eqs.) was added in one portion. The solution was then warmed to 65° C. and 4-fluorobenzylamine (1.2 eqs) was added at 65-68° C. The mixture was then aged at reflux for 7 hours. The solution was cooled to 55° C., and acetic acid (2 eqs.) was added in one portion. Water was added followed by seed crystals of 2. (Note: Crystallization would occur without seed, but seeding provides a more reliable method of crystal growth.) The resultant slurry was aged at 60° C. with the addition of more water during the ageing. The slurry was then cooled to 20° C., filtered, washed with 1:1 methanol:water, and dried in a nitrogen stream to give compound 2 (96 wt. % purity by HPLC assay, 1.75 wt. % water by Karl Fisher titration), 98% overall yield (corrected for purity).

Compound 2:

$^1$H NMR (600.13 MHz, CDCl₃) δ 12.37 (br s, 2H), 7.95 (br t, J=6 Hz, 1H), 735-7.31 (m, 2H), 7.25-7.19 (br m, 5H), 7.08-7.04 (m, 2H), 6.49 (s, 1H), 4.96 (s, 2H), 4.58 (d, J=6.0 Hz, 2H), 1.64 (s, 6H).

$^{13}$C NMR (150.92 MHz, CDCl₃) δ 168.5, 162.6 (d, $J_{CF}$=246.6 Hz), 160.0, 1553, 154.1, 147.9, 136.5, 133.1 (d, $J_{CF}$=3.1 Hz), 129.7 (d, $J_{CF}$=7.9 Hz), 128.6, 128.1, 127.9, 127.1, 116.0 (d, $J_{CF}$=22.0 Hz), 66.8, 55.5, 42.7, 26.7.

Step 2: Preparation of benzyl 1-(4-{[(4-fluorobenzyl)amino]carbonyl}-5-hydroxy-1-methyl-6-oxo-1,6-dihydropyrimidin-2-yl)-1-methylethylcarbamate (Compound 3)

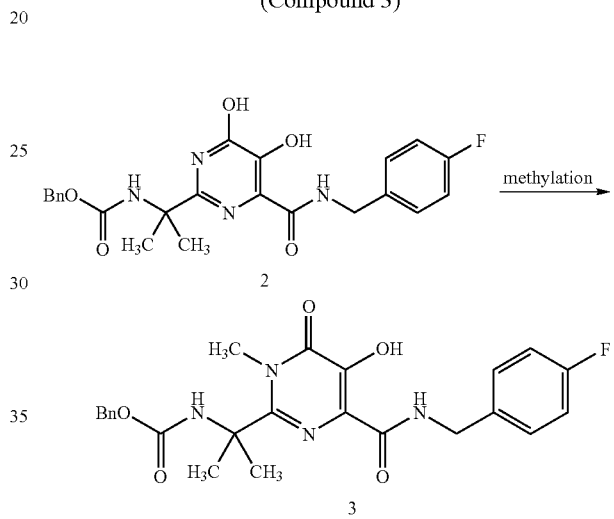

NMP (~1.73 mL per gram of 2) was charged at 20-25° C. to a jacketed glass reactor equipped with a mechanical overhead stirrer, a thermocouple probe, and a condenser. Compound 2 (1 eq.), Mg(OH)₂ (2 eqs.), Me₃SO⁺I⁻ (2 eqs.), and water (0.6 eq.) were then added sequentially to the reactor while maintaining the temperature at 20-25° C., after which the resulting mixture was degassed by passage of nitrogen through the head space of the agitated mixture for 5 minutes at 30° C. Upon completion of the degassing, the nitrogen source to the reaction flask was disconnected and the reaction vented through the condenser to nitrogen. The mixture was then warmed to 97° C. over 1.5 hours, wherein an exotherm was observed when the temperature reached 97° C. causing the temperature to rise to about 109° C. The mixture was maintained at 97-102° C. for 5 hours. The mixture was then cooled to 26° C. and degassed methanol (~1.73 mL per gram of 2) was added, followed by the addition of 5 N aqueous HCl (~0.86 mL per gram of 2). The mixture was then aged for 30 minutes, after which an aqueous solution of NaHSO₃ (0.03 eq.) was added. Seed crystals of compound 3 were then added. (Note: Crystallization would occur without seed, but seeding provides a more reliable method of crystal growth.) The mixture was aged for 1 hour at 36-40° C., and then degassed 5 N aqueous HCl (0.86 mL per gram of 2) was added. The mixture was cooled to 10° C., aqueous NaHSO₃ (0.03 eq.) was added, and the mixture gradually cooled to 10° C., after which the slurry was filtered and the resulting filter cake was washed with a 1:1 methanol:water mixture. The white granular crystalline product was dried to a constant weight under a stream of nitrogen to give compound 3 (99 wt % purity by HPLC assay), 89% overall yield (corrected for purity).

Compound 3:

(Spectra Acquired at 0° C.-Major Carbamate Rotamer Reported)

$^1$H NMR (600.13 MHz, CDCl$_3$) δ 11.95 (s, 1H), 7.83 (t, J=6.0 Hz, 1H), 7.36-7.28 (overlapping m, 7H), 7.07-7.03 (m, 2H), 5.42 (s, 1H), 5.00 (s, 2H), 4.57 (d, J=6.0 Hz, 2H), 3.65 (s, 3H), 1.67 (s, 6H)

$^{13}$C NMR (150.92 MHz, CDCl$_3$) δ 168.5, 162.4 (d, J$_{CF}$=246.0 Hz), 159.8, 154.5, 151.1, 146.7, 135.9, 133.1 (d, J$_{CF}$=3.1 Hz), 129.6 (d, J$_{CF}$=7.9 Hz), 128.8, 128.7, 128.4, 124.4, 115.9 (d, J$_{CF}$=21.4 Hz), 67.2, 57.3, 42.5, 33.1, 28.1.

Steps 3 & 4: Preparation of 2-(1-amino-1-methyl-ethyl)-N-(4-fluorobenzyl)-1-methyl-6-oxo-5-pivaly-loxy-1,6-dihydropyrimidine-4-carboxamide (Compound 5)

resulting slurry was cooled to 10° C., after which pivaloyl chloride (1.2 eqs.) was added over about 30 minutes while maintaining the reaction temperature at 10-15° C. After the addition was completed, the slurry was aged 15 minutes at 10-15° C. Water (1 mL per gram of 3) was then added and the mixture aged for 30 minutes while allowing it to warm to room temperature, after which the lower aqueous layer was cut.

Methanol (2 mL/gram of 3) and glycolic acid (1.2 eqs.) were added to the organic layer and the crude mixture hydrogenated at 5 psig and 25° C. using 5% Pd/C (2.3 wt. % with respect to 3, 50% wet) for 4 hours. The catalyst was filtered off, using a small celite plug, and the cake washed with methanol (1 mL/gram of 3). The filtrates were combined and charged into a round bottom flask to which triethylamine (1.3 eqs.) was then added in one portion at room temperature. Water (3 mL/gram of 3) was then added over 1 hour at room temperature, the slurry aged for 2 hours, and filtered. The filter cake was washed with 1:1 methanol:water and dried using N$_2$ flow to give compound 5 (99 wt. % purity by HPLC assay), 94% overall yield (corrected for purity).

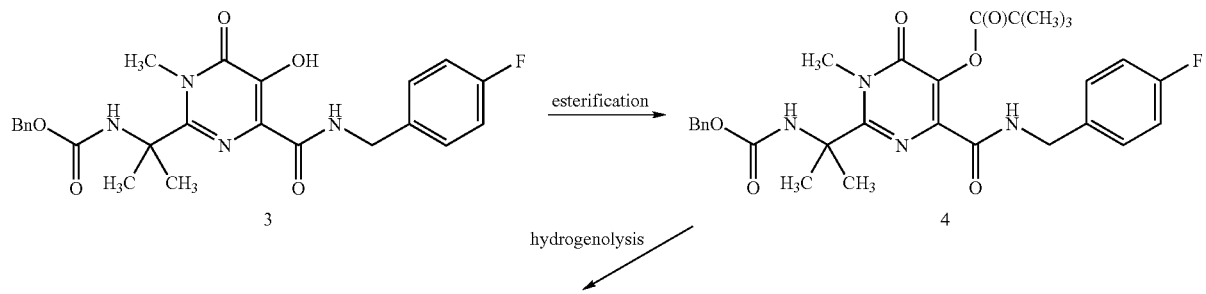

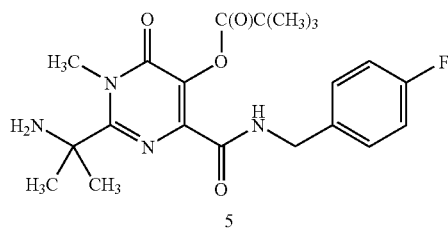

A round bottom flask was charged at room temperature with Compound 3 (1.0 eq.) and ethyl acetate (3 mL per gram of 3), after which triethylamine (1.3 eqs.) was added in one portion, followed by the addition of DMAP (0.001 eq.) The Compound 5:

$^1$H NMR (600.13 MHz, CDCl$_3$) δ 7.88 (br t, J=6.0 Hz, 1H), 7.29-7.25 (m, 2H), 7.04-7.00 (m, 2H), 4.53 (d, J=6.0 Hz, 2H), 4.01 (s, 3H), 1.60 (br s, 2H), 1.59 (s, 6H), 1.43 (s, 9H).

$^{13}$C NMR (150.92 MHz, CDCl$_3$) δ 175.9, 162.4 (d, $J_{CF}$=246.0 Hz), 161.9, 160.5, 160.4, 138.8, 136.6, 133.9 (d, $J_{CF}$=3.1 Hz), 129.4 (d, $J_{CF}$=7.9 Hz), 115.8 (d, $J_{CF}$=21.4 Hz), 56.5, 42.6, 39.4, 34.4, 31.3, 27.3.

Step 5: Preparation of Compound A

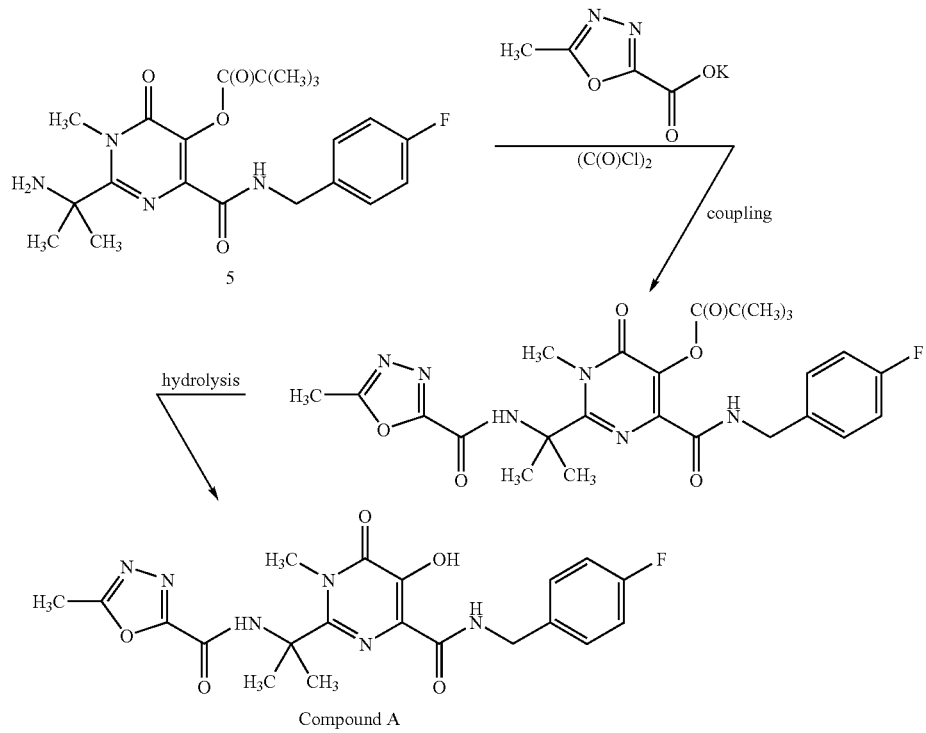

A flask was charged with oxadiazole K-salt (1.15 eqs.), acetonitrile (~5.5 mL/gram of oxadiazole K-salt) and DMF (~12.1 µL/gram of oxadiazole K-salt). The mixture was cooled to −5° C. and oxalyl chloride (1.10 eqs.) added over 30 minutes with stirring and with venting of CO and CO$_2$ evolving from the mixture. The slurry was aged at 0 to 5° C. for 1 hour and cooled to −10° C. to await the addition of free amine 5.

A separate flask was charged with free amine 5 (1.00 eq.) and acetonitrile (1.5 mL/gram of 5). The solution was cooled to −10° C. and N-methylmorpholine (1.20 eqs.) was added. The free amine/NMM slurry was added to the oxadiazole acid chloride slurry at −10° C. over 45 minutes. After coupling was completed as determined by HPLC, 20% aqueous potassium hydroxide (5.8 eqs.) was added and the reaction mixture aged at 0° C. to 5° C. until the hydrolysis of the pivalate ester was complete as determined by HPLC. Acetic acid (10.0 eqs.) was then added over 5 minutes and the reaction mixture was allowed to warm to 15° C. Water (8 mL/gram of 5) was then added slowly and seed crystal was added. (Note: Crystallization would occur without seed, but seeding provides a more reliable method of crystal growth.) The slurry was aged for 1 hour, after which the product slurry was filtered and washed with 2.5:1 water/acetonitrile, then with water, and then dried to afford Compound A (>99 wt % by HPLC assay), 97% overall yield.

HPLC assay conditions: Column=Zorbax SB Phenyl (15 cm×4.6 mm); flow rate=1.0 mL/minute; temperature=15° C.; detection=UV at 220 nm; Solvents: A=Acetonitrile, B 0.1M aqueous H$_3$PO$_4$; gradient elution from 25% A:75% B to 40% A:60% B over 3 minutes, to gradient elution to 45% A:55% B over 5 minutes to gradient elution over 9 minutes to 90% A:10% B, to gradient elution to 95% A:5% B over 3 minutes.

Compound A:
$^1$H NMR (399.87 MHz, CDCl$_3$) δ 12.04 (s, 1H), 8.45 (s, 1H), 7.94 (t, J=6.2 Hz, 1H), 7.41-7.36 (m, 2H), 7.08-7.02 (m, 2H), 4.61 (d, J=6.2 Hz, 2H), 3.68 (s, 3H), 2.63 (s, 3H), 1.87 (s, 6H).
$^{13}$C NMR (100.55 MHz, CDCl$_3$) δ 168.3, 166.7, 162.6 (d, $J_{CF}$=245.7 Hz), 159.6, 159.1, 152.0, 150.4, 147.2, 133.4 (d, $J_{CF}$=3.2 Hz), 129.9 (d, $J_{CF}$=8.0 Hz), 124.1, 115.9 (d, $J_{CF}$=21.7 Hz), 58.0, 42.7, 33.5, 26.7, 11.4.

While the foregoing specification teaches the principles of the present invention, with examples provided for the purpose of illustration, the practice of the invention encompasses all of the usual variations, adaptations and/or modifications that come within the scope of the following claims. All publications, patents and patent applications cited herein are incorporated by reference in their entirety into the disclosure.

What is claimed is:
1. A process for preparing a compound of Formula I:

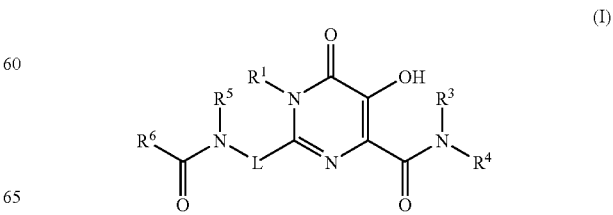

which comprises:
(A) contacting a compound of Formula II:

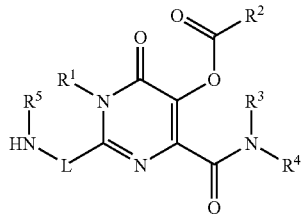

(II)

with an acylating agent of Formula III:

(III)

in an aprotic organic solvent and in the presence of base to obtain an acylated amine compound of Formula IV:

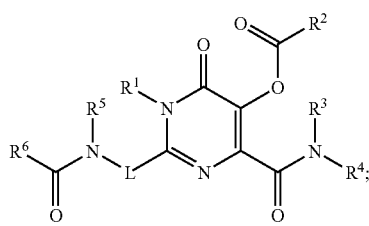

(IV)

and
(B) contacting the compound of Formula IV with an aqueous base in an aprotic organic solvent to obtain the compound of Formula I; wherein:
X is halogen or $OC(O)R^6$;
$R^1$ is $C_{1-6}$ alkyl or $C_{1-6}$ alkyl substituted with AryA;
$R^2$ is $C_{1-8}$ alkyl or AryB;
$R^3$ is H or $C_{1-6}$ alkyl;
$R^4$ is $C_{1-6}$ alkyl substituted with AryC;
AryC is phenyl or naphthyl, wherein the phenyl or naphthyl is optionally substituted with from 1 to 4 substituents each of which is independently:
(1) $C_{1-6}$ alkyl,
(2) $C_{3-6}$ cycloalkyl,
(3) $C_{1-6}$ haloalkyl,
(4) O—$C_{1-6}$ alkyl,
(5) O—$C_{1-6}$ haloalkyl,
(6) O—$C_{3-6}$ cycloalkyl,
(7) S—$C_{1-6}$ alkyl,
(8) S—$C_{1-6}$ haloalkyl,
(9) S—$C_{3-6}$ cycloalkyl,
(10) halo,
(11) CN,
(12) $NO_2$,
(13) $N(H)R^E$,
(14) N(—$C_{1-6}$ alkyl)$_2$,
(15) CH(O),
(16) C(O)—$C_{1-6}$ alkyl,
(17) C(O)O—$C_{1-6}$ alkyl,
(18) C(O)$NH_2$,
(19) C(O)N(H)—$C_{1-6}$ alkyl,
(20) C(O)N(—$C_{1-6}$ alkyl)$_2$,
(21) $C_{1-6}$ alkyl substituted with:
  (a) O—$C_{1-6}$ alkyl,
  (b) O—$C_{1-6}$ haloalkyl,
  (c) O—$C_{3-6}$ cycloalkyl,
  (d) S—$C_{1-6}$ alkyl,
  (e) CN,
  (f) $NO_2$,
  (g) $N(H)R^E$,
  (h) N(—$C_{1-6}$ alkyl)$_2$,
  (i) CH(O),
  (j) C(O)—$C_{1-6}$ alkyl,
  (k) C(O)O—$C_{1-6}$ alkyl,
  (l) C(O)$NH_2$,
  (m) C(O)N(H)—$C_{1-6}$ alkyl, or
  (n) C(O)N(—$C_{1-6}$ alkyl)$_2$, or
(22) AryQ, with the proviso that no more than one of the optional substituents is AryQ;
AryA independently has the same definition as AryC;
AryB independently has the same definition as AryC;
L is $C_{1-6}$ alkylene;
$R^5$ is H or $C_{1-6}$ alkyl;
$R^6$ is:
(1) HetP,
(2) $C_{1-6}$ alkyl substituted with HetP,
(3) C(O)—$C_{1-6}$ alkylene-HetP,
(4) C(O)—HetP,
(5) CycQ,
(6) O-CycQ,
(7) C(O)-CycQ,
(8) C(O)O-CycQ,
(9) AryQ,
(10) O-AryQ,
(11) C(O)-AryQ,
(12) C(O)O-AryQ,
(13) HetQ,
(14) O-HetQ,
(15) C(O)—HetQ, or
(16) C(O)O-HetQ;
$R^E$ is a branched $C_{3-6}$ alkyl;
HetP is a 4- to 7-membered saturated or mono-unsaturated heterocyclic ring containing 1 N atom through which the ring is attached to the rest of the compound and optionally containing an additional heteroatom wherein the additional heteroatom is selected from N, O, and S; wherein the optional S in the ring is optionally in the form of S(O) or S(O)$_2$ and the optional N in the ring is substituted with $C_{1-6}$ alkyl, C(O)—$C_{1-6}$ alkyl, or C(O)O—$C_{1-6}$ alkyl when the ring is saturated and is part of the ring double bond when the ring is mono-unsaturated;
CycQ is a $C_{3-7}$ cycloalkyl which is optionally substituted with from 1 to 3 substituents each of which is independently halogen, $C_{1-6}$ alkyl, $C_{1-6}$ haloalkyl, O—$C_{1-6}$ alkyl, O—$C_{1-6}$ haloalkyl, oxo, N($C_{1-6}$ alkyl)$_2$, C(O)N($C_{1-6}$ alkyl)$_2$, C(O)—$C_{1-6}$ alkyl, or C(O)O—$C_{1-6}$ alkyl;
each AryQ is independently phenyl which is optionally substituted with from 1 to 4 substituents each of which is independently halogen, CN, $NO_2$, $C_{1-6}$ alkyl, $C_{1-6}$ haloalkyl, O—$C_{1-6}$ alkyl, O—$C_{1-6}$ haloalkyl, S—$C_{1-6}$ alkyl, N($C_{1-6}$ alkyl)$_2$, C(O)N($C_{1-6}$ alkyl)$_2$, C(O)—$C_{1-6}$ alkyl, or C(O)O—$C_{1-6}$ alkyl; and
HetQ is a heteroaryl which is a 5- or 6-membered heteroaromatic ring containing from 1 to 4 heteroatoms independently selected from N, O and S, to which is optionally fused a benzene ring; wherein the heteroaryl is optionally substituted with from 1 to 4 substituents each of which is independently halogen, CN, NO$_2$, C$_{1-6}$ alkyl, C$_{1-6}$ haloalkyl, O—C$_{1-6}$ alkyl, O—C$_{1-6}$ haloalkyl, S—C$_{1-6}$ alkyl, N(—C$_{1-6}$ alkyl)$_2$, C(O)N(—C$_{1-6}$ alkyl)$_2$, C(O)—C$_{1-6}$ alkyl, or C(O)O—C$_{1-6}$ alkyl.

2. The process according to claim 1, which further comprises:

(C) contacting a compound of Formula V:

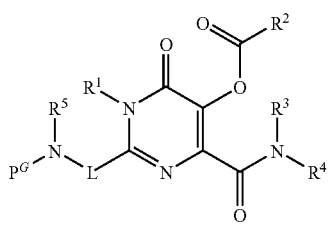
(V)

in organic solvent C with a source of hydrogen in the presence of a hydrogenolysis catalyst to obtain the compound of Formula II; wherein P$^G$ is an amine protective group capable of being cleaved by hydrogenolysis, wherein organic solvent C is selected from a carboxylic ester, an aliphatic ether or diether, a cyclic ether or diether, an aromatic hydrocarbon, a tertiary carboxylic amide, an alcohol, an alcohol-water mixture, or an alcohol-water-carboxylic ester mixture.

3. The process according to claim 1, which further comprises:

(D) contacting a compound of Formula VI:

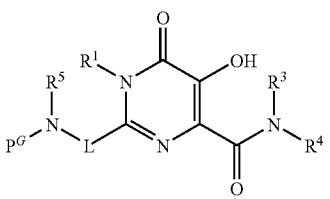
(VI)

with an esterification agent of Formula VII:

(VII)

in organic solvent D in the presence of base and optionally in the presence of an esterification catalyst to obtain the compound of Formula V; wherein Y is halogen or OC(O)R$^2$, wherein organic solvent D is selected from a carboxylic ester, an aliphatic ether or diether, a cyclic ether or diether, an aromatic hydrocarbon, a tertiary carboxylic amide, an alcohol, an alcohol-water mixture, or an alcohol-water-carboxylic ester mixture.

4. The process according to claim 3, which further comprises:

(E) contacting a compound of Formula VIII:

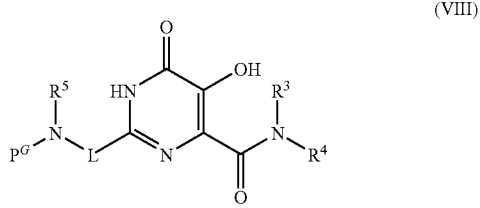
(VIII)

with an alkylating agent in a polar aprotic solvent, in the presence of a magnesium base, and optionally in the presence of water to obtain the compound of Formula VI; wherein the alkylating agent is:

(1) provided that R$^1$ is methyl, a compound of formula (CH$_3$)$_3$S(O)I, (2) provided that R$^1$ is methyl, a compound of formula (CH$_3$)$_3$S(O)Z, wherein Z is Cl or Br, (3) a compound of formula R$^1$—I, (4) a compound of formula (R$^1$)$_2$SO$_4$, or (5) a compound of formula R$^1$-Q, wherein Q is an alkyl sulfonate or an aryl sulfonate;

and provided that when the alkylating agent is (CH$_3$)$_3$S(O)Z, (R$^1$)$_2$SO$_4$, or R$^1$-Q, the agent is employed in combination with an iodide source.

5. A process according to claim 1, which is a process for preparing Compound A:

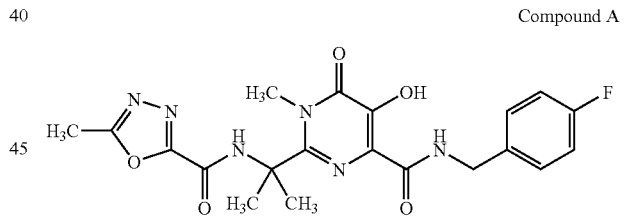
Compound A which comprises:

(A') contacting a compound of Formula II-A:

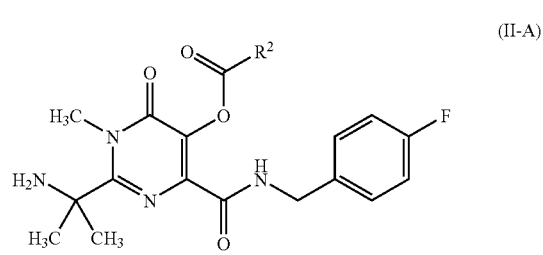
(II-A)

with an acylating agent of Formula III-A:

(III-A)

in organic solvent A' in the presence of base to obtain an acylated amine compound of Formula IV-A:

(IV-A)

and (B') contacting the compound of Formula IV-A with an aqueous base in organic solvent B' to obtain Compound A; wherein X is halogen; and $R^2$ is $C_{1-8}$ alkyl or phenyl, wherein organic solvent A' is acetonitrile, THF, DMF, DMAC, MTBE or NMP and organic solvent B' is acetonitrile, THF, DMF, MTBE or NMP.

6. The process according to claim 5, wherein X is Cl or Br, and $R^2$ is branched $C_{3-6}$ alkyl or phenyl.

7. The process according to claim 6, wherein $R^2$ is t-butyl.

8. The process according to claim 5, which further comprises:

(C') contacting a compound of Formula V-A:

(V-A)

in organic solvent C' with a source of hydrogen and in the presence of a hydrogenolysis catalyst to obtain the compound of Formula II-A; wherein $P^G$ is an amine protective group capable of being cleaved by hydrogenolysis, wherein organic solvent C' is ethyl acetate, isopropyl acetate, diethyl ether, MTBE, DME, dimethoxymethane, bis(2-methoxyethyl) ether, THF, dioxolane, dioxane, toluene, DMF, DMAC, NMP, methanol, ethanol, isopropanol, n-propanol, isobutanol, methanol-water, ethanol-water, or methanol-ethyl acetate-water.

9. The process according to claim 8, wherein $P^G$ is allyloxycarbonyl, benzyloxycarbonyl, p-methoxybenzyloxycarbonyl, p-nitrobenzyloxycarbonyl, p-bromobenzyloxycarbonyl, p-chlorobenzyloxycarbonyl, or 2,4-dichlorobenzyloxycarbonyl.

10. The process according to claim 9, wherein $P^G$ is benzyloxycarbonyl.

11. The process according to claim 8, which further comprises:

(D') contacting a compound of Formula VI-A:

(VI-A)

with an esterification agent of Formula VII:

(VII)

in organic solvent D' in the presence of base and optionally in the presence of an esterification catalyst to obtain the compound of Formula V-A; wherein Y is halogen or $OC(O)R^2$, wherein organic solvent D' is ethyl acetate, isopropyl acetate, diethyl ether, MTBE, DME, dimethoxymethane, bis(2-methoxyethyl)ether, THF, dioxolane, dioxane, toluene, DMF, DMAC, NMP, methanol, ethanol, isopropanol, n-propanol, isobutanol, methanol-water, ethanol-water, or methanol-ethyl acetate-water.

12. The process according to claim 11, which further comprises:

(E') contacting a compound of Formula VIII-A:

(VIII-A)

with a methylating agent in organic solvent E', in the presence of a magnesium base, and optionally in the presence of water, to obtain the compound of Formula VI-A; wherein the methylating agent is: (1) $(CH_3)_3S(O)I$, (2) $(CH_3)_3S(O)Z$, wherein Z is Cl or Br, (3) $CH_3I$, (4) $(CH_3)_2SO_4$ in combination with an iodide source, or (5) a compound of formula $CH_3$-Q, wherein Q is an alkyl sulfonate or an aryl sulfonate; and provided that when the methylating agent is $(CH_3)_3S(O)Z$, $(CH_3)_2SO_4$, or $CH_3$-Q, then the agent is employed in combination with an iodide source, wherein organic solvent E' is diethyl ether, MTBE, DME, DMM, bis(2-methoxyethyl)ether, THF, dioxolane, dioxane, acetonitrile, propionitrile, benzonitrile, o-tolunitrile, p-tolunitrile, triethylamine, diisopropylethylamine, N methylpyrrolidine, N-methylpiperidine, N-methylmorpholine, DMF, DMAC, NMP, sulfolane, DMPU, or HMPA.

13. The process according to claim 12, wherein the alkylating agent is $(CH_3)_3S(O)I$ and the base is $Mg(OH)_2$, MgO, or $Mg(O-t-Bu)_2$.

14. The process according to claim 5, wherein
X is Cl;
R² is t-butyl;
Step A' and Step B' are conducted in the same pot wherein organic solvent A' and organic solvent B' are the same solvent;
Step A' is conducted at a temperature in a range of from about −15° C. to about 15° C.;
organic solvent A' is acetonitrile, THF, DMF, MTBE, DMAC, or NMP;
the base employed in Step A' is NMM, NEM, TEA, DIPEA, or DABCO;
the acylating agent of Formula III-A is employed in an amount in a range of from about 1 to about 2 equivalents per equivalent Compound II-A.
the base in Step A' is employed in an amount in a range of from about 1 to about 2 equivalents per equivalent of Compound II-A;
Step A' is optionally conducted in the presence of an activating agent;
Step B' is conducted at a temperature in a range of from about −5° C. to about 15° C.;
the aqueous base employed in Step B' is an alkali metal hydroxide; and
the aqueous base is employed in Step B' in an amount in a range of from about 1 to about 8 equivalents per equivalent of the compound of Formula IV.

15. A process for preparing Compound A:

Compound A which comprises:
(A″) contacting a compound of Formula ii-a:

ii-a in acetonitrile with at least about 1 equivalent per equivalent of compound ii-a of an acylating agent of Formula iii-a:

iii-a and in the presence of at least about 1 equivalent of NMM per equivalent of compound ii-a at a temperature in a range of from about −15° C. to about 15° C. to obtain an acylated amine of Formula iv-a:

iv-a and
(B″) contacting the acylated amine iv-a with at least about 1 equivalent of aqueous KOH per equivalent of compound ii-a in acetonitrile at a temperature in a range of from about −5° C. to about 15° C. to obtain Compound A.

16. The process according to claim 15, wherein Step A″ and Step B″ are conducted in the same pot, wherein Step B″ comprises adding the aqueous KOH to the reaction mixture resulting from Step A″ and adjusting as necessary the temperature of the admixture to be in the range of from about −5° C. to about 15° C.

17. The process according to claim 15, which further comprises:
(C″) contacting a compound of Formula v-a:

v-a with a source of hydrogen in methanol optionally in admixture with water or with water and ethyl acetate, in the presence of a supported or unsupported Pd or Pd salt as catalyst, and in the presence of at least about 1 equivalent of glycolic acid per equivalent of compound v-a, to obtain the compound of Formula ii-a.

18. The process according to claim 17, which further comprises:
(D″) contacting a compound of Formula vi-a:

vi-a with at least about 1 equivalent of pivaloyl chloride per equivalent of compound vi-a in ethyl acetate at a temperature in a range of from about 0° C. to about 30° C., in the presence of at least about 1 equivalent of triethylamine per equivalent of compound vi-a and in the presence of an esterification catalyst selected from DMAP, DBN and DBU, to obtain the compound of Formula v-a.

19. The process according to claim 18, wherein compound v-a is recovered from the Step D" reaction mixture as a slurry, suspension or solution in ethyl acetate which is used directly in Step C".

20. The process according to claim 18, which further comprises:

(E") contacting a compound of Formula viii-a:

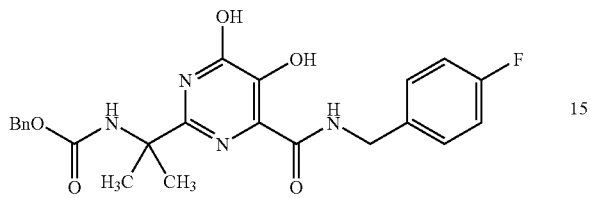

viii-a with at least about 1 equivalent of $(CH_3)_3S(O)I$ per equivalent of compound viii-a in NMP at a temperature in a range of from about 95° C. to about 110° C., in the presence of at least about 1 equivalent of $Mg(OH)_2$ per equivalent of compound viii-a and in the presence of at least about 0.1 equivalent of water per equivalent of compound viii-a, to obtain a compound of Formula vi-a.

21. A compound having the formula:

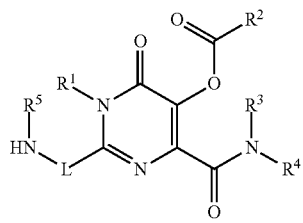

(II)

wherein
L is $C_{1-6}$ alkylene;
$R^1$ is $C_{1-6}$ alkyl or $C_{1-6}$ alkyl substituted with AryA;
$R^2$ is $C_{1-8}$ alkyl or AryB;
$R^3$ is H or $C_{1-6}$ alkyl;
$R^4$ is $C_{1-6}$ alkyl substituted with AryC;
$R^5$ is H or $C_{1-6}$ alkyl;
  AryC is phenyl or naphthyl, wherein the phenyl or naphthyl is optionally substituted with from 1 to 4 substituents each of which is independently:
   (1) $C_{1-6}$ alkyl,
   (2) $C_{3-6}$ cycloalkyl,
   (3) $C_{1-6}$ haloalkyl,
   (4) O—$C_{1-6}$ alkyl,
   (5) O—$C_{1-6}$ haloalkyl,
   (6) O—$C_{3-6}$ cycloalkyl,
   (7) S—$C_{1-6}$ alkyl,
   (8) S—$C_{1-6}$ haloalkyl,
   (9) S—$C_{3-6}$ cycloalkyl,
   (10) halo,
   (11) CN,
   (12) $NO_2$,
   (13) $N(H)R^E$,
   (14) N(—$Cl_{1-6}$ alkyl)$_2$,
   (15) CH(O),
   (16) C(O)—$C_{1-6}$ alkyl,
   (17) C(O)O—$C_{1-6}$ alkyl,
   (18) $C(O)NH_2$,
   (19) C(O)N(H)—$C_{1-6}$ alkyl,
   (20) C(O)N(—$C_{1-6}$ alkyl)$_2$,
   (21) $C_{1-6}$ alkyl substituted with:
     (a) O—$C_{1-6}$ alkyl,
     (b) O—$C_{1-6}$ haloalkyl,
     (c) O—$C_{3-6}$ cycloalkyl,
     (d) S—$C_{1-6}$ alkyl,
     (e) CN,
     (f) $NO_2$,
     (g) $N(H)R^E$,
     (h) N(—$C_{1-6}$ alkyl)$_2$,
     (i) CH(O),
     (j) C(O)—$C_{1-6}$ alkyl,
     (k) C(O)O—$C_{1-6}$ alkyl,
     (l) $C(O)NH_2$,
     (m) C(O)N(H)—$C_{1-6}$ alkyl, or
     (n) C(O)N(H)—$C_{1-6}$ alkyl)$_2$, or
   (22) AryQ, with the proviso that no more than one of the optional substituents is AryQ;
AryA independently has the same definition as AryC;
AryB independently has the same definition as AryC;
$R^E$ is a branched $C_{3-6}$ alkyl;
each AryQ is independently phenyl which is optionally substituted with from 1 to 4 substituents each of which is independently halogen, CN, $NO_2$, $C_{1-6}$ alkyl, $C_{1-6}$ haloalkyl, O—$C_{1-6}$ alkyl, O—$C_{1-6}$ haloalkyl, S—$C_{1-6}$ alkyl, N($C_{1-6}$ alkyl)$_2$, C(O)N($C_{1-6}$ alkyl)$_2$, C(O)—$C_{1-6}$alkyl, or C(O)O—$C_{1-6}$ alkyl.

22. The compound according to claim 21, or a pharmaceutically acceptable salt thereof, wherein $R^2$ is a branched $C_{3-6}$ alkyl.

23. A compound which is selected from the group consisting of:

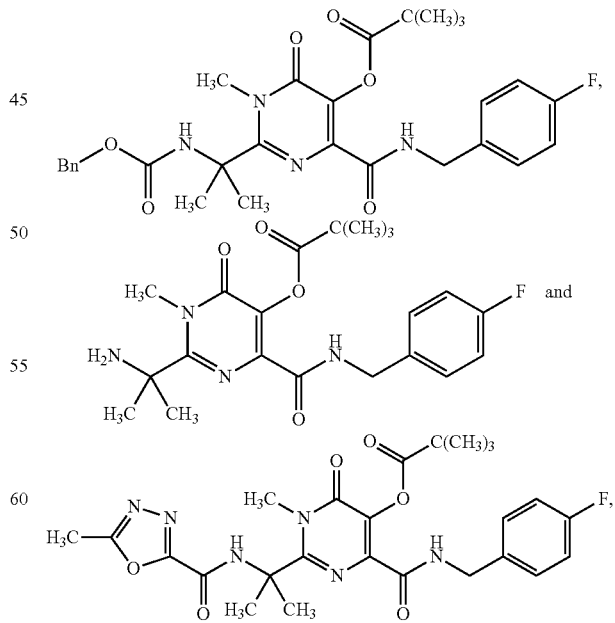

and pharmaceutically acceptable salts thereof.

24. A compound having the formula:

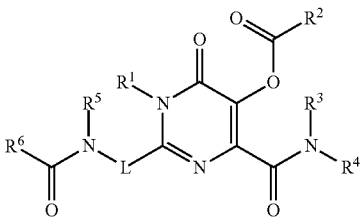

(IV)

and pharmaceutically acceptable salts thereof,
wherein:
L is $C_{1-6}$ alkylene;
$R^1$ is $C_{1-6}$ alkyl or $C_{1-6}$ alkyl substituted with AryA;
$R^2$ is $C_{1-8}$ alkyl or AryB;
$R^3$ is H or $C_{1-6}$ alkyl;
$R^4$ is $C_{1-6}$ alkyl substituted with AryC;
$R^5$ is H or $C_{1-6}$ alkyl;
$R^6$ is:
  (1) HetP,
  (2) $C_{1-6}$ alkyl substituted with HetP,
  (3) C(O)—$C_{1-6}$ alkylene-HetP,
  (4) C(O)—HetP,
  (5) CycQ,
  (6) O-CycQ,
  (7) C(O)-CycQ,
  (8) C(O)O-CycQ,
  (9) AryQ,
  (10) O-AryQ,
  (11) C(O)-AryQ,
  (12) C(O)O-AryQ,
  (13) HetQ,
  (14) O-HetQ,
  (15) C(O)—HetQ, or
  (16) C(O)O-HetQ;
AryC is phenyl or naphthyl, wherein the phenyl or naphthyl is optionally substituted with from 1 to 4 substituents each of which is independently:
  (1) $C_{1-6}$ alkyl,
  (2) $C_{3-6}$ cycloalkyl,
  (3) $C_{1-6}$ haloalkyl,
  (4) O—$C_{1-6}$ alkyl,
  (5) O—$C_{1-6}$ haloalkyl,
  (6) O—$C_{3-6}$ cycloalkyl,
  (7) S—$C_{1-6}$ alkyl,
  (8) S—$C_{1-6}$ haloalkyl,
  (9) S—$C_{3-6}$ cycloalkyl,
  (10) halo,
  (11) CN,
  (12) $NO_2$,
  (13) N(H)$R^E$,
  (14) N(—$C_{1-6}$ alkyl)$_2$,
  (15) CH(O),
  (16) C(O)—$C_{1-6}$ alkyl,
  (17) C(O)O—$C_{1-6}$ alkyl,
  (18) C(O)$NH_2$,
  (19) C(O)N(H)—$C_{1-6}$ alkyl,
  (20) C(O)N(—$C_{1-6}$ alkyl)$_2$,
  (21) $C_{1-6}$ alkyl substituted with:
    (a) O—$C_{1-6}$ alkyl,
    (b) O—$C_{1-6}$ haloalkyl,
    (c) O—$C_{3-6}$ cycloalkyl,
    (d) S—$C_{1-6}$ alkyl,
    (e) CN,
    (f) $NO_2$,
    (g) N(H)$R^E$,
    (h) N(—$C_{1-6}$ alkyl)$_2$,
    (i) CH(O),
    (j) C(O)—$C_{1-6}$ alkyl,
    (k) C(O)O—$C_{1-6}$ alkyl,
    (l) C(O)$NH_2$,
    (m) C(O)N(H)—$C_{1-6}$ alkyl, or
    (n) C(O)N(—$C_{1-6}$ alkyl)$_2$, or
  (22) AryQ, with the proviso that no more than one of the optional substituents is AryQ;
AryA independently has the same definition as AryC;
AryB independently has the same definition as AryC;
$R^E$ is a branched $C_{3-6}$ alkyl;
HetP is a 4- to 7-membered saturated or mono-unsaturated heterocyclic ring containing 1N atom through which the ring is attached to the rest of the compound and optionally containing an additional heteroatom wherein the additional heteroatom is selected from N, O, and S; wherein the optional S in the ring is optionally in the form of S(O) or S(O)$_2$ and the optional N in the ring is substituted with $C_{1-6}$ alkyl, C(O)—$C_{1-6}$ alkyl, or C(O)O—$C_{1-6}$ alkyl when the ring is saturated and is part of the ring double bond when the ring is mono-unsaturated;
CycQ is a $C_{3-7}$ cycloalkyl which is optionally substituted with from 1 to 3 substituents each of which is independently halogen, $C_{1-6}$ alkyl, $C_{1-6}$ haloalkyl, O—$C_{1-6}$ alkyl, O—$C_{1-6}$ haloalkyl, oxo, N($C_{1-6}$ alkyl)$_2$, C(O)N($C_{1-6}$ alkyl)$_2$, C(O)—$C_{1-6}$ alkyl, or C(O)O—$C_{1-6}$ alkyl;
each AryQ is independently phenyl which is optionally substituted with from 1 to 4 substituents each of which is independently halogen, CN, $NO_2$, $C_{1-6}$ alkyl, $C_{1-6}$ haloalkyl, O—$C_{1-6}$ alkyl, O—$C_{1-6}$ haloalkyl, S—$C_{1-6}$ alkyl, N($C_{1-6}$ alkyl)$_2$, C(O)N($C_{1-6}$ alkyl)$_2$, C(O)—$C_{1-6}$ alkyl, or C(O)O—$C_{1-6}$ alkyl; and
HetQ is a heteroaryl which is a 5- or 6-membered heteroaromatic ring containing from 1 to 4 heteroatoms independently selected from N, O and S, to which is optionally fused a benzene ring; wherein the heteroaryl is optionally substituted with from 1 to 4 substituents each of which is independently halogen, CN, $NO_2$, $C_{1-6}$ alkyl, $C_{1-6}$ haloalkyl, O—$C_{1-6}$ alkyl, O—$C_{1-6}$ haloalkyl, S—$C_{1-6}$ alkyl, N(—$C_{1-6}$ alkyl)$_2$, C(O)N(—$C_{1-6}$ alkyl)$_2$, C(O)—$C_{1-6}$ alkyl, or C(O)O—$C_{1-6}$ alkyl.

25. A compound having the formula:

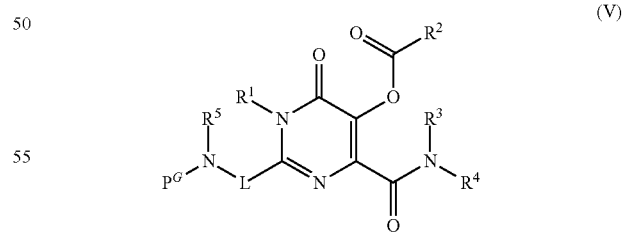

(V)

and pharmaceutically acceptable salts thereof
wherein:
L is $C_{1-6}$ alkylene;
$R^1$ is $C_{1-6}$ alkyl or $C_{1-6}$ alkyl substituted with AryA;
$R^2$ is $C_{1-8}$ alkyl or AryB;
$R^3$ is H or $C_{1-6}$ alkyl;
$R^4$ is $C_{1-6}$ alkyl substituted with AryC;
$R^5$ is H or $C_{1-6}$ alkyl;

AryC is phenyl or naphthyl, wherein the phenyl or naphthyl is optionally substituted with from 1 to 4 substituents each of which is independently:
(1) $C_{1-6}$ alkyl,
(2) $C_{3-6}$ cycloalkyl,
(3) $C_{1-6}$ haloalkyl,
(4) O—$C_{1-6}$ alkyl,
(5) O—$C_{1-6}$ haloalkyl,
(6) O—$C_{3-6}$ cycloalkyl,
(7) S—$C_{1-6}$ alkyl,
(8) S—$C_{1-6}$ haloalkyl,
(9) S—$C_{3-6}$ cycloalkyl,
(10) halo,
(11) CN,
(12) $NO_2$,
(13) N(H)$R^E$,
(14) N(—$Cl_{1-6}$ alkyl)$_2$,
(15) CH(O),
(16) C(O)—$C_{1-6}$ alkyl,
(17) C(O)O—$C_{1-6}$ alkyl,
(18) C(O)$NH_2$,
(19) C(O)N(H)—$C_{1-6}$ alkyl,
(20) C(O)N(—$C_{1-6}$ alkyl)$_2$,
(21) $C_{1-6}$ alkyl substituted with:
   (a) O—$C_{1-6}$ alkyl,
   (b) O—$C_{1-6}$ haloalkyl,
   (c) O—$C_{3-6}$ cycloalkyl,
   (d) S—$C_{1-6}$ alkyl,
   (e) CN,
   (f) $NO_2$,
   (g) N(H)$R^E$,
   (h) N(—$C_{1-6}$ alkyl)$_2$,
   (i) CH(O),
   (j) C(O)—$C_{1-6}$ alkyl,
   (k) C(O)O—$C_{1-6}$ alkyl,
   (l) C(O)$NH_2$,
   (m) C(O)N(H)—$C_{1-6}$ alkyl, or
   (n) C(O)N(H)—$C_{1-6}$ alkyl)$_2$, or
(22) AryQ, with the proviso that no more than one of the optional substituents is AryQ;
AryA independently has the same definition as AryC;
AryB independently has the same definition as AryC;
$R^E$ is a branched $C_{3-6}$ alkyl;
each AryQ is independently phenyl which is optionally substituted with from 1 to 4 substituents each of which is independently halogen, CN, $NO_2$, $C_{1-6}$ alkyl, $C_{1-6}$ haloalkyl, O—$C_{1-6}$ alkyl, O—$C_{1-6}$ haloalkyl, S—$C_{1-6}$ alkyl, N($C_{1-6}$ alkyl)$_2$, C(O)N($C_{1-6}$ alkyl)$_2$, C(O)—$C_{1-6}$ alkyl, or C(O)O—$C_{1-6}$ alkyl.

26. The compound according to claim 24, or a pharmaceutically acceptable salt thereof, wherein $R^2$ is a branched $C_{3-6}$ alkyl.

27. The compound according to claim 25, or a pharmaceutically acceptable salt thereof, wherein $R^2$ is a branched $C_{3-6}$ alkyl.

\* \* \* \* \*